United States Patent [19]

Krause

[11] Patent Number: 5,077,506

[45] Date of Patent: Dec. 31, 1991

[54] MICROPROCESSOR CONTROLLED ARTHROSCOPIC SURGICAL SYSTEM

[75] Inventor: Kenneth W. Krause, Sandown, N.H.

[73] Assignee: Dyonics, Inc., Andover, Mass.

[21] Appl. No.: 306,434

[22] Filed: Feb. 3, 1989

[51] Int. Cl.⁵ ............................................. H02P 5/50
[52] U.S. Cl. .................................... 318/71; 318/67; 388/815; 606/1
[58] Field of Search .................. 318/35, 49–50, 318/51–53, 66–70, 71; 128/303 R, 303.13; 388/809, 810, 815, 821–822, 833

[56] References Cited

U.S. PATENT DOCUMENTS

| | | | |
|---|---|---|---|
| 4,055,786 | 10/1977 | DiMarzio | 318/685 X |
| 4,388,582 | 6/1983 | Saar et al. | 370/20 |
| 4,634,942 | 1/1987 | Naroto | 318/375 X |
| 4,641,069 | 2/1987 | Fujioka | 318/51 X |
| 4,644,232 | 2/1987 | Nojiri et al. | 318/66 |
| 4,689,541 | 8/1987 | Jones et al. | 318/685 X |
| 4,705,038 | 11/1987 | Sjostrom et al. | 128/305 |
| 4,827,195 | 5/1989 | Newell et al. | 318/49 |

Primary Examiner—William M. Shoop, Jr.
Assistant Examiner—David Martin
Attorney, Agent, or Firm—Kirkpatrick & Lockhart

[57] ABSTRACT

An apparatus for controlling the speed of a plurality of DC motors, comprises a device for supplying voltage to one of the plurality of DC motors, first selector for selecting one of the DC motors to be connected to the device for supplying voltage, second selector for selecting a desired speed for the selected DC motor, a device for producing a feedback signal representative of an electrical current drawn by the selected DC motor and a controller for: (i) producing a reference voltage in response to the first and second selectors (ii) producing a load voltage in response to the feedback signal and (iii) outputting a control signal which is the sum of the reference voltage and the load voltage to the device for supplying voltage so that the selected DC motor is operated at the desired speed.

27 Claims, 13 Drawing Sheets

MICROPROCESSOR CONTROLLED ARTHROSCOPIC SURGICAL SYSTEM

BACKGROUND OF THE INVENTION

1. Field of the Invention

The present invention is directed generally to the automatic control of DC motors and, more specifically, to the automatic control of arthroscopic surgical instruments powered by DC motors.

2. Description of the Prior Art

Surgical devices for cutting and abrading tissue come in widely different sizes and configurations, each designed for performance of a particular surgical procedure Each surgical device differs with respect to the speed and torque at which it can safely operate. If a surgical procedure on a patient requires use of surgical devices of differing characteristics, the surgeon must either have separate motorized units for each device or a central unit must be adjusted with each device change. The adjustment of a central unit is a time-consuming operation and one that entails some risk of error with possible damage to the device or injury to the patient.

U.S. Pat. No. 4,705,038 to Sjostrom et al. discloses a single-motor surgical system for operating a set of various surgical devices having different operational limits The system includes a handpiece containing a motor. The handpiece is adapted to alternately receive a proximal portion of each of several surgical devices, each device having an indicator on its proximal portion that denotes its operational limits. The handpiece includes an automatic sensor for sensing the indicator. Discrete electronic controls responsive to the sensor automatically establish the operational limits of the motor in accordance with the respective surgical device received by the handpiece.

A disadvantage of the system disclosed in U.S. Pat. No. 4,705,038 is that the discrete electronic circuit which provides the system control has limitations with respect to the degree of precision with which the motor can be controlled Additionally, the discrete electronic circuit is not easily or inexpensively modified to operate additional surgical devices each of which has distinct operating limits. Accordingly, the need exists for a system which can provide enhanced control capabilities and which can be easily and inexpensively adapted to accommodate various types of surgical devices.

SUMMARY OF THE INVENTION

The present invention is directed to a system for controlling powered surgical instruments within predetermined parameters, comprising means for supplying voltage to one of a plurality of hand-held surgical motors, first means for selectively connecting one of the surgical motors to the means for supplying voltage, second means for selecting a desired speed for the connected surgical motor, means for producing a feedback signal representative of an electrical current drawn by the connected surgical motor and control means for: (i) selecting a reference voltage in response to the connected surgical motor and the desired speed (ii) producing a load voltage in response to the feedback signal and the connected surgical motor and (iii) outputting a control signal responsive to the reference voltage and the load voltage to the means for supplying voltage so that the connected surgical motor is operated within predetermined parameters.

The present invention is also directed to an apparatus for controlling the speed of a plurality of DC motors, comprising means for supplying voltage to one of the plurality of DC motors, first means for selecting one of the DC motors to be connected to the means for supplying voltage, second means for selecting a desired speed for the selected DC motor, means for producing a feedback signal representative of an electrical current drawn by the selected DC motor and control means for: (i) producing a reference voltage in response to the first and second means for selecting (ii) producing a load voltage in response to the feedback signal and the first means for selecting and (iii) outputting a control signal which is the sum of the reference voltage and the load voltage to the means for supplying voltage so that the selected DC motor is operated at the desired speed.

The system of the present invention is able to meet the needs for both providing enhanced control capabilities and the ability to easily and inexpensively adapt the system to accommodate various types of surgical devices These and other advantages and benefits of the present invention will become apparent from the description of a preferred embodiment hereinbelow.

BRIEF DESCRIPTION OF THE DRAWINGS

In order that the present invention may be clearly understood and readily practiced, preferred embodiments will now be described, by way of example only, with reference to the accompanying figures wherein:

FIG. 4I depicts a flow chart illustrating the steps of subroutine STATUS performed by the microprocessor of the system of FIG. 1;

DETAILED DESCRIPTION OF THE PREFERRED EMBODIMENTS

To aid the reader in understanding the present invention, the description thereof is divided into the following sections:
A. SYSTEM CONFIGURATION
B. SYSTEM OPERATION
  1. Motor Selection and Initialization
  2. Control Routines
    a. Oscillate
    b. Reverse
    c. Forward
    d. Diagnostic Status
    e. Slow Down/Oscillate
    f. Slow Down/Reverse
    g. Slow Down/Forward
    h. Slow Down
    i. Speed Up/Oscillate
    i. Speed Up/Reverse
    j. Speed Up/Forward
    k. Speed Up
    l. No Action

A. SYSTEM CONFIGURATION

Figure 1:
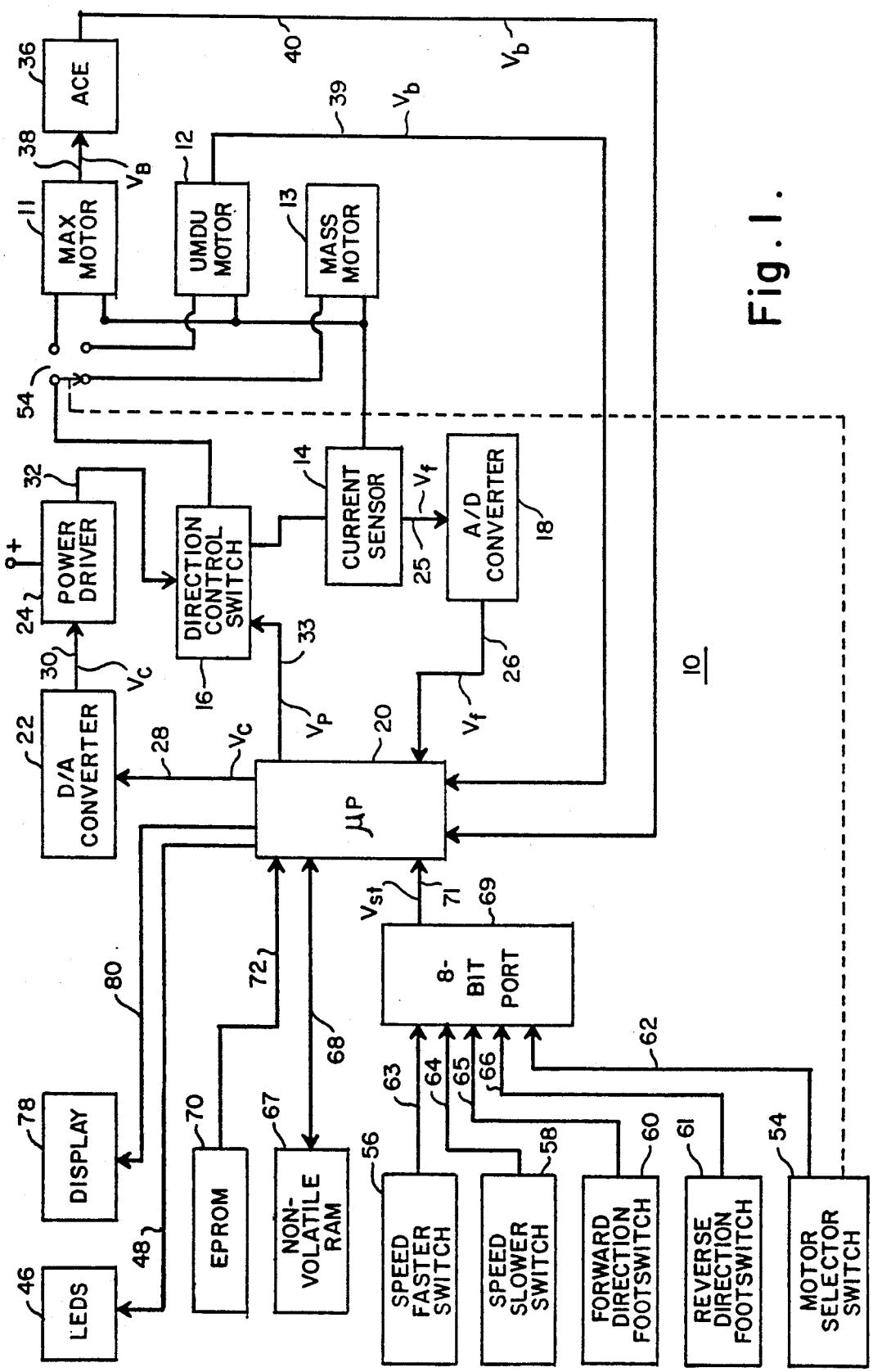
FIG. 1 illustrates, in block diagram form, a microprocessor controlled system for powered surgical instruments constructed according to the teachings of the present invention.

FIG. 1 illustrates, in block diagram form, a microprocessor controlled system for powered surgical instruments 10 constructed according to the teachings of the present invention Like reference numerals are employed among the various figures to designate like elements Throughout the discussion which follows, all numeric values may be assumed to be in decimal (base ten) notation unless otherwise noted. Although the present invention is described in an embodiment wherein surgical instruments are being controlled, the principles of the present invention may be applied to other environments such as controlling a plurality of tools at a robotic workstation.

A motor control loop consists of one of motors 11, 12 or 13, a motor selector switch 54, a current sensor 14, a direction control switch 16 which may be an H-switch, an eight-bit analog-to-digital converter 18, a microprocessor 20, a ten-bit digital-to-analog converter 22 and power driver circuitry 24. A feedback signal $V_f$ from the current sensor 14, which is representative of the electrical current drawn by whichever motor 11, 12 or 13 is operatively connected to the motor control loop, is input to the analog-to-digital converter 18 through input line 25. A digital output signal, which is a digital representation of the feedback signal $V_f$, is produced by the analog-to-digital converter 18. That digital signal $V_f$ is input to microprocessor 20 through input line 26. The microprocessor 20 calculates, based on the feedback signal $V_f$, a desired operating voltage and produces a control signal $V_c$ representative of that operating voltage. That control signal $V_c$ is output to digital-to-analog converter 22 through output line 28. An analog output signal which is an analog representation of the control signal $V_c$ is produced by the digital-to-analog converter 22. That analog control signal $V_c$ is output to power driver circuitry 24 through output line 30. Power driver circuitry 24 provides the appropriate supply voltage to one of the motors 11, 12 or 13 through output line 32, direction control switch 16 and motor selector switch 54. The microprocessor 20 provides a polarity signal $V_p$ to direction control switch 16 through output line 33.

Figure 2:
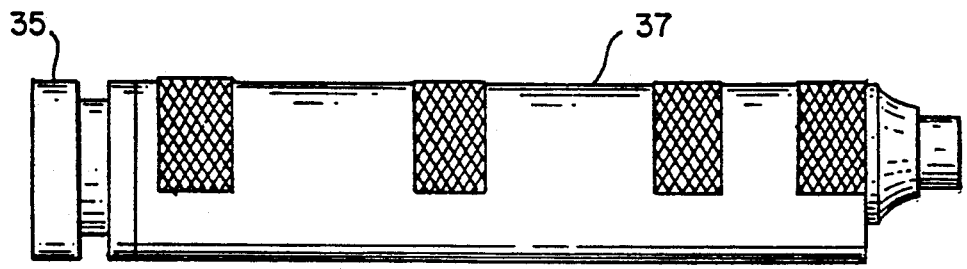
FIG. 2 illustrates a side-view of a handpiece containing a motor used in conjunction with the system of FIG. 1.
Figure 2A:
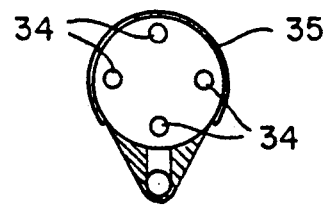
FIG. 2A illustrates an end-view of the handpiece of FIG. 2.

Blade sensors 34 are radially oriented about a blade interface 35 of handpiece 37 as shown in FIGS. 2 and 2A. Handpiece 37 contains one of the motors 11, 12 or 13. The number of blade sensors 34 oriented about the blade interface 35 is a function of the type of motor which is incorporated into the handpiece 37. The handpiece 37 may include the motor 11 which is specifically designed to be used with the system 10 of FIG. 1 and shall be denoted throughout this discussion as "the MAX motor". The MAX motor 11 includes four Hall-effect devices as blade sensors 34 mounted in blade interface 35. The four Hall-effect devices may be oriented about the blade interface 35 at 90° intervals. Another handpiece 37 may be used with the present invention which includes the motor 12, which may be a universal type motor hereinafter denoted as "the UMDU motor", in which case the interface 35 includes two reed switches as blade sensors 34. The motor 13, which may be a mini-motor hereinafter denoted as "the MASS motor", may be incorporated into a third handpiece 37 in which case no blade sensors 34 are located in the interface 35.

A blade code signal $V_b$ is produced by the sensors 34 as a result of the sensors, interaction with an arthroscopic blade 42 as described hereinbelow. That blade code signal $V_b$ is available at the outputs of the blade sensors 34 and is (i) either shifted out of the blade sensors 34, received by an asynchronous communications element "ACE" 36 (shown in FIG. 1) through input line 38 and then input to microprocessor 20 through input line 40 in the case of the MAX motor 11, or (ii) is input directly to the microprocessor 20 through input line 39 in the case of the UMDU motor 12.

Figure 3:
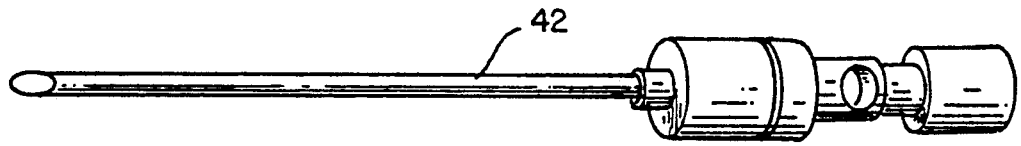
FIG. 3 illustrates a perspective view of an arthroscopic surgical blade used in conjunction with the system of FIG. 1.
Figure 3A:
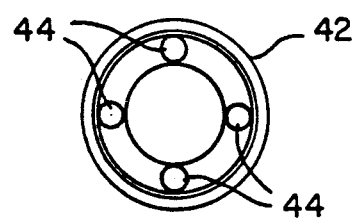
FIG. 3A illustrates an end-view of the arthroscopic surgical blade of FIG. 3.

Arthroscopic blades 42 shown in FIGS. 3 and 3A may contain either a maximum of two or four magnets 44 radially oriented about the blade 42 at either 180° intervals in the two magnet arrangement or 90° intervals in the four magnet arrangement. The number, position and polarity of the magnets 4 describe a code unique to each blade 42. The maximum number of magnets 44 mounted on each blade 42 is dependent upon the type of motor 11, 12 or 13 with which the blade 42 is to be used. Each type of motor 11, 12 or 13 has a unique number of modes in which it can operate. The MASS motor 13 has only one mode of operation and the interface 35 (shown in FIGS. 2 and 2A), therefore, has no sensors 34 as indicated above. The UMDU motor 12 has four modes of operation and thus the interface 35 has two sensors 34. The MAX motor 11 has forty-nine modes of operation and the interface 35 includes four sensors 34 as explained earlier. It follows that arthroscopic blades 42 used with the MASS motor 13 do not contain any magnets 44; arthroscopic blades 42 used with the UMDU motor 12 have two magnets 44; and arthroscopic blades 42 used with the MAX motor 1 have four magnets 44. The magnets 44 may alternatively be located in an adaptor (not shown) which receives the proximal portion of the arthroscopic blade 42 and connects with the interface 35.

LEDs 46 shown in FIG. 1 are driven by the microprocessor 20 through output line 48. The appropriate LED segments 46 are illuminated to display the speed range, the current operating speed, and the relative position of the current operating speed between maximum and minimum speeds for the particular arthroscopic blade 42 in use. A sixteen character by one line fluorescent display 78 connected to microprocessor 20 through output line 80 indicates all pertinent status conditions and blade identification information.

Motor selector switch 54, speed faster switch 56, speed slower switch 58, forward direction footswitch 60 and reverse direction footswitch 61 communicate with the microprocessor 20 through input lines 62, 63, 64, 65 and 66, respectively, and eight-bit input port 69. A switch status signal $V_{st}$ is available from the eight-bit input port 69 and is input to microprocessor 20 through input line 71.

Non-volatile random access memory chip 67 performs a permanent memory function and is used to store the last operating speed of each arthroscopic blade 42. A battery (not shown) powers the random access memory chip 67 which may have a capacity of two kilobytes. The memory chip 67 is connected to microprocessor 20 through input/output line 68. An EPROM chip 70 stores the control unit software and blade data and communicates with microprocessor 20 through input line 72. The EPROM chip 70 may have a capacity of thirty-two kilobytes.

B. SYSTEM OPERATION

1. Motor Selection and Initialization

Figure 4A:
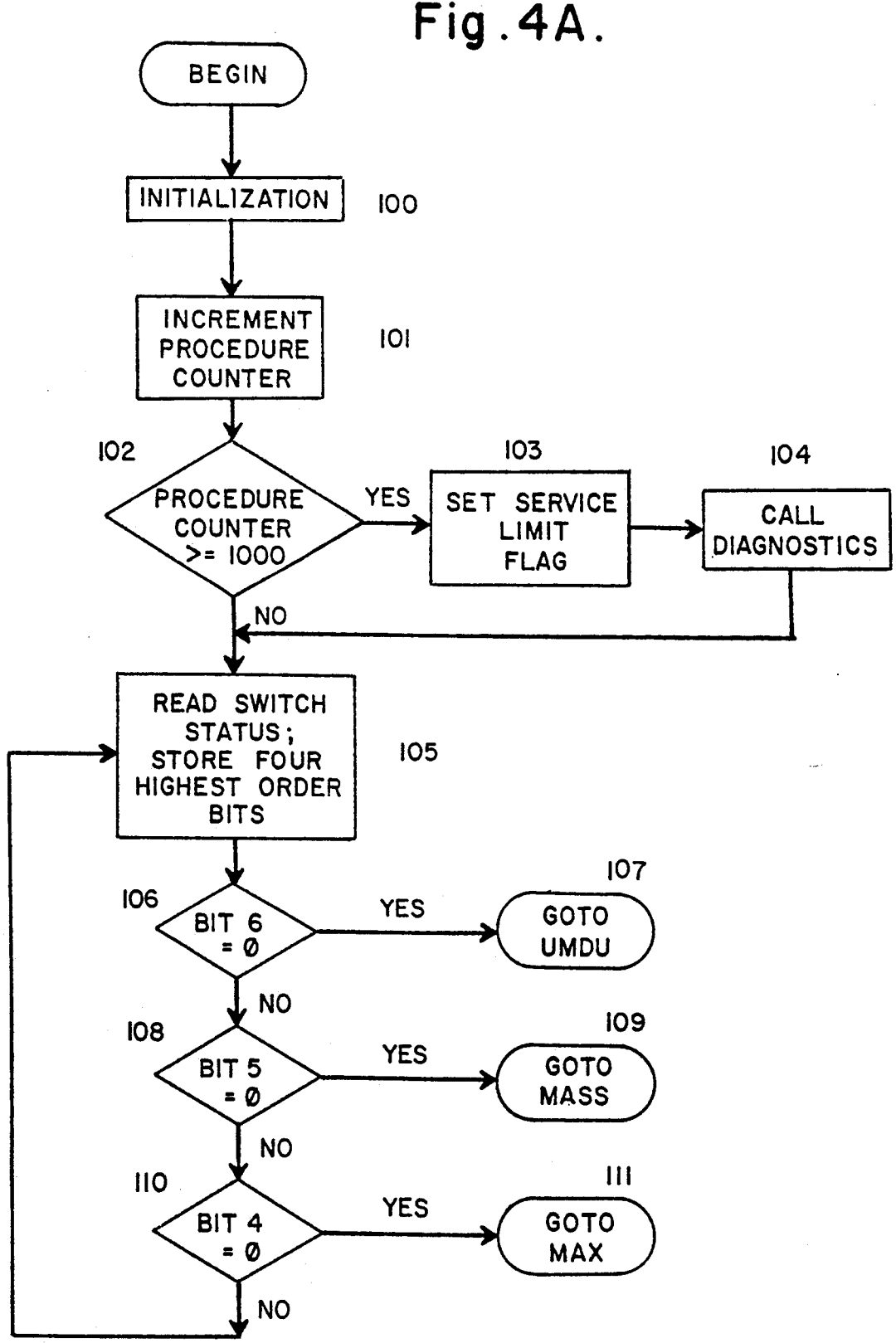
FIG. 4A depicts a flow chart illustrating the steps of the main routine BEGIN performed by the microprocessor of the system of FIG. 1.
Figure 4B:
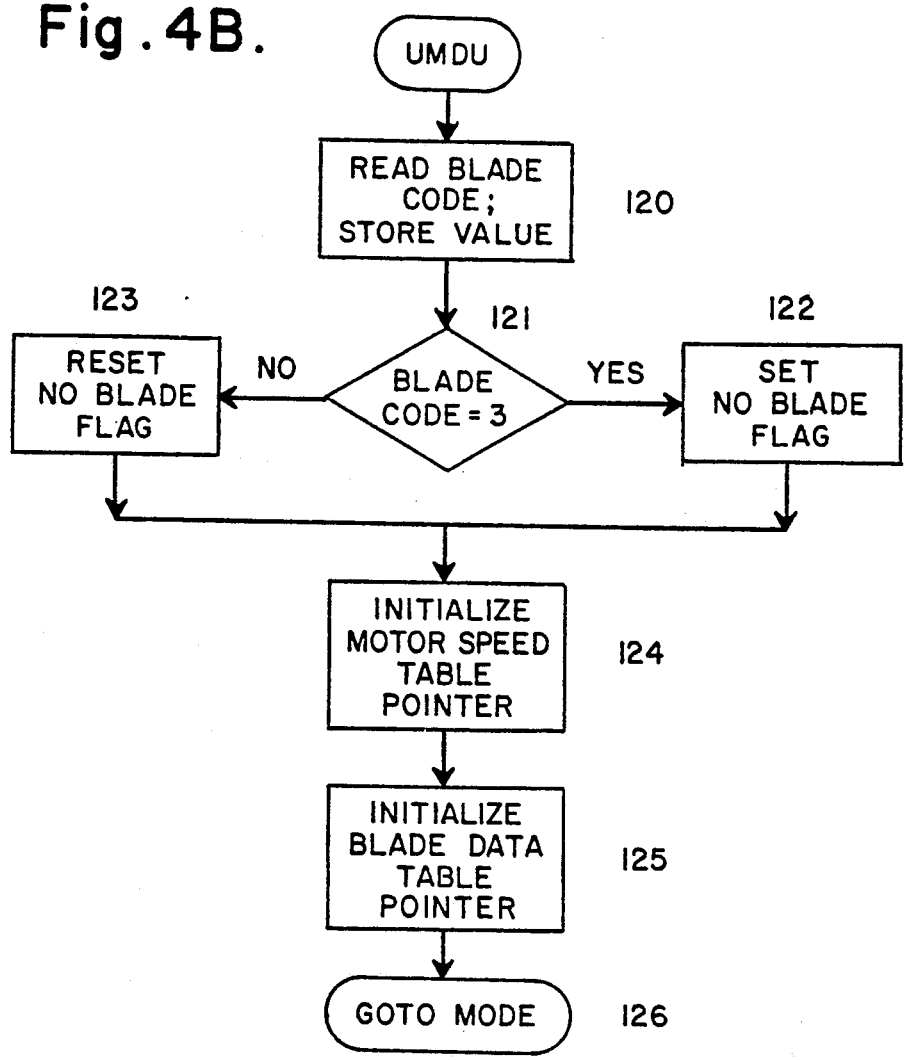
FIG. 4B depicts a flow chart illustrating the steps of motor initialization routine UMDU performed by the microprocessor of the system of FIG. 1.
Figure 4C:
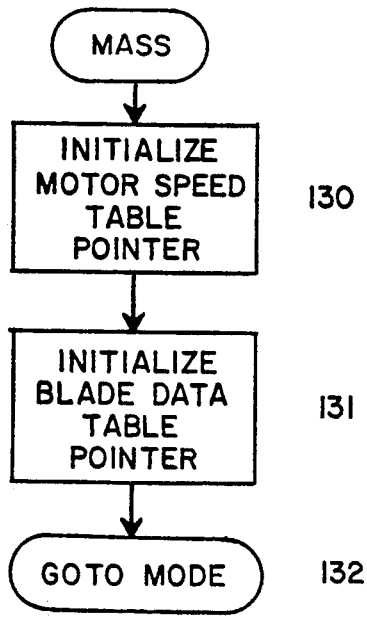
FIG. 4C depicts a flow chart illustrating the steps of motor initialization routine MASS performed by the microprocessor of the system of FIG. 1.
Figure 4D:
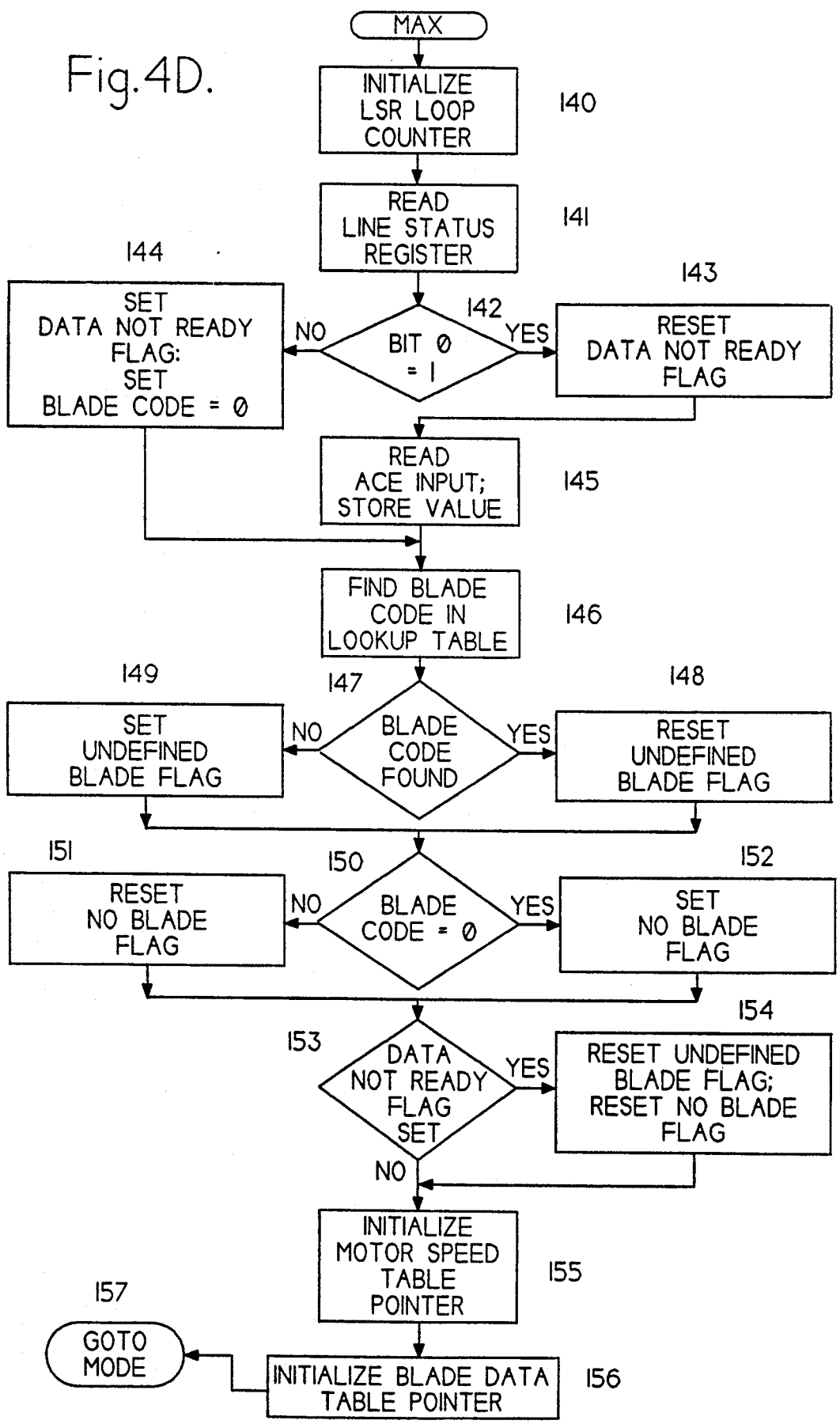
FIG. 4D depicts a flow chart illustrating the steps of motor initialization routine MAX performed by the microprocessor of the system of FIG. 1.
Figure 4E:
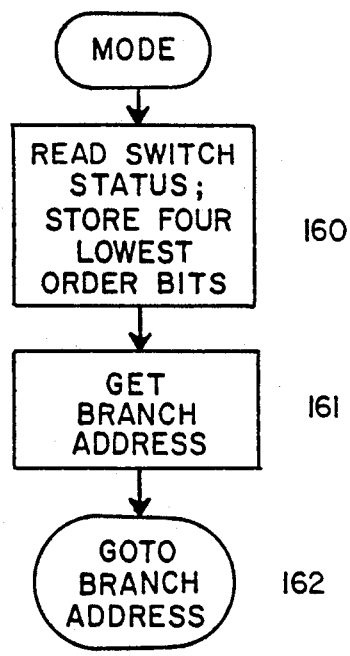
FIG. 4E depicts a flow chart illustrating the steps of branch control routine MODE performed by the microprocessor of the system of FIG. 1.
Figure 4L:
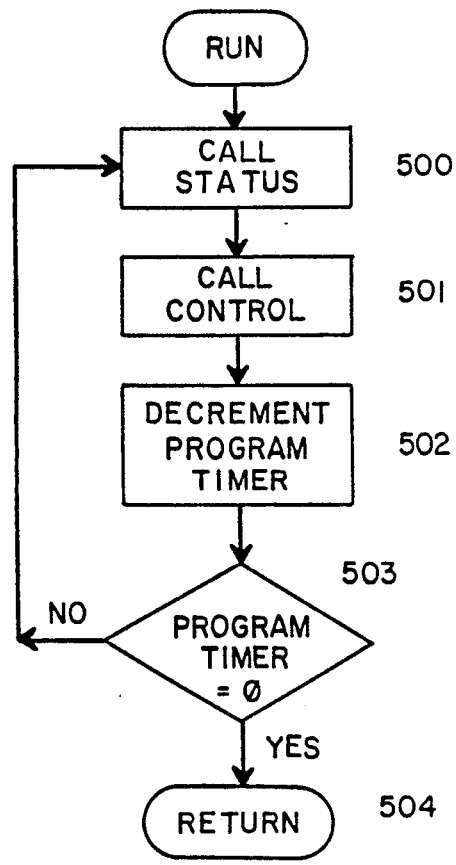
FIG. 4L depicts a flow chart illustrating the steps of subroutine RUN performed by the microprocessor of the system of FIG. 1.
Figure 4J:
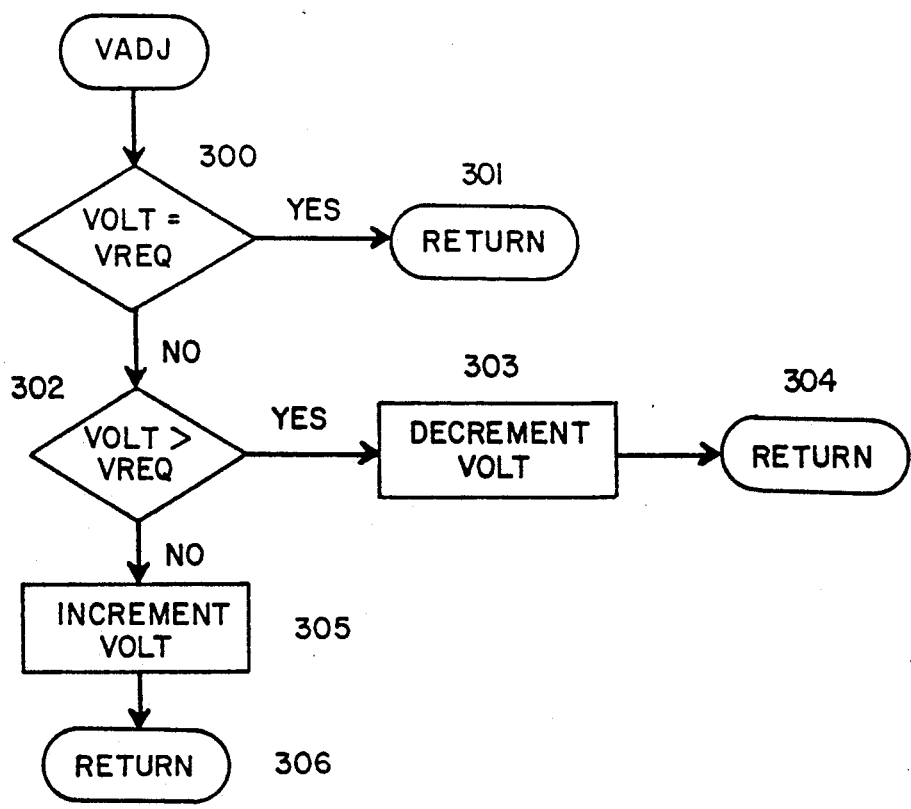
FIG. 4J depicts a flow chart illustrating the steps of subroutine VADJ performed by the microprocessor of the system of FIG. 1.
Figure 4F:
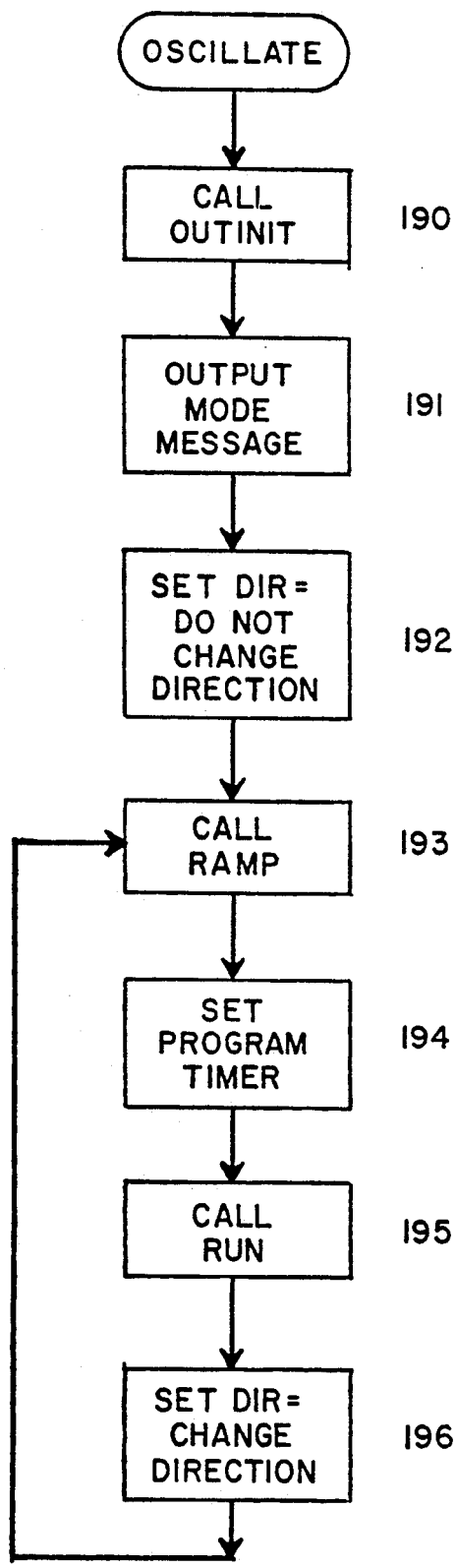
FIG. 4F depicts a flow chart illustrating the steps of motor control routine OSCILLATE performed by the microprocessor of the system of FIG. 1.
Figure 4G:
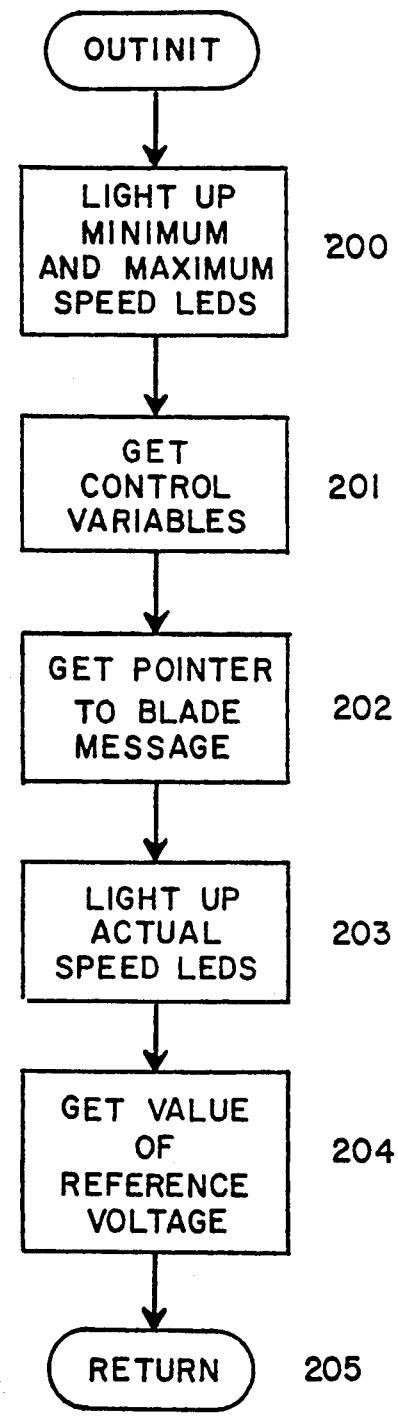
FIG. 4G depicts a flow chart illustrating the steps of subroutine OUTINIT performed by the microprocessor of the system of FIG. 1.
Figure 4H:
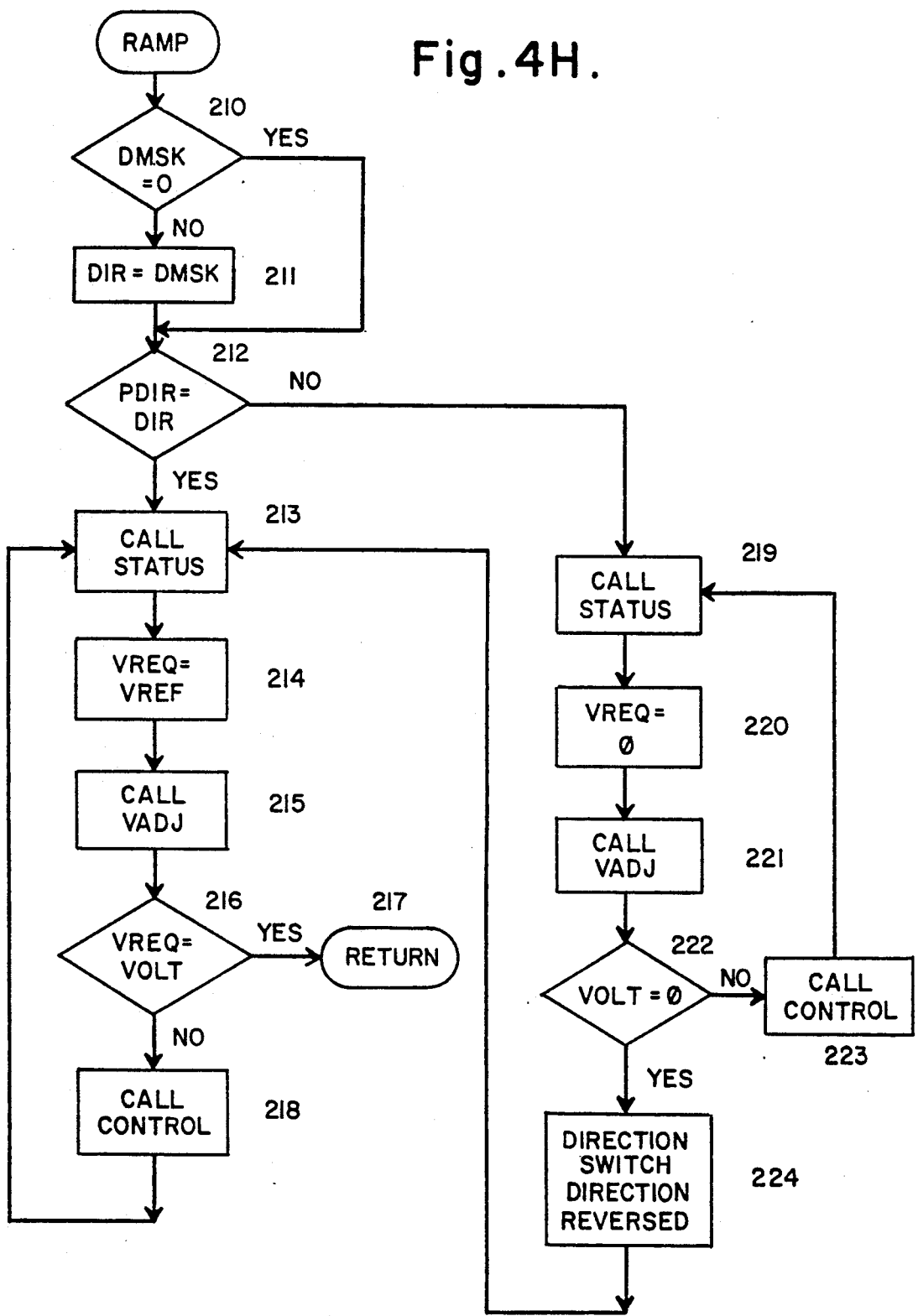
FIG. 4H depicts a flow chart illustrating the steps of subroutine RAMP performed by the microprocessor of the system of FIG. 1.
Figure 41:
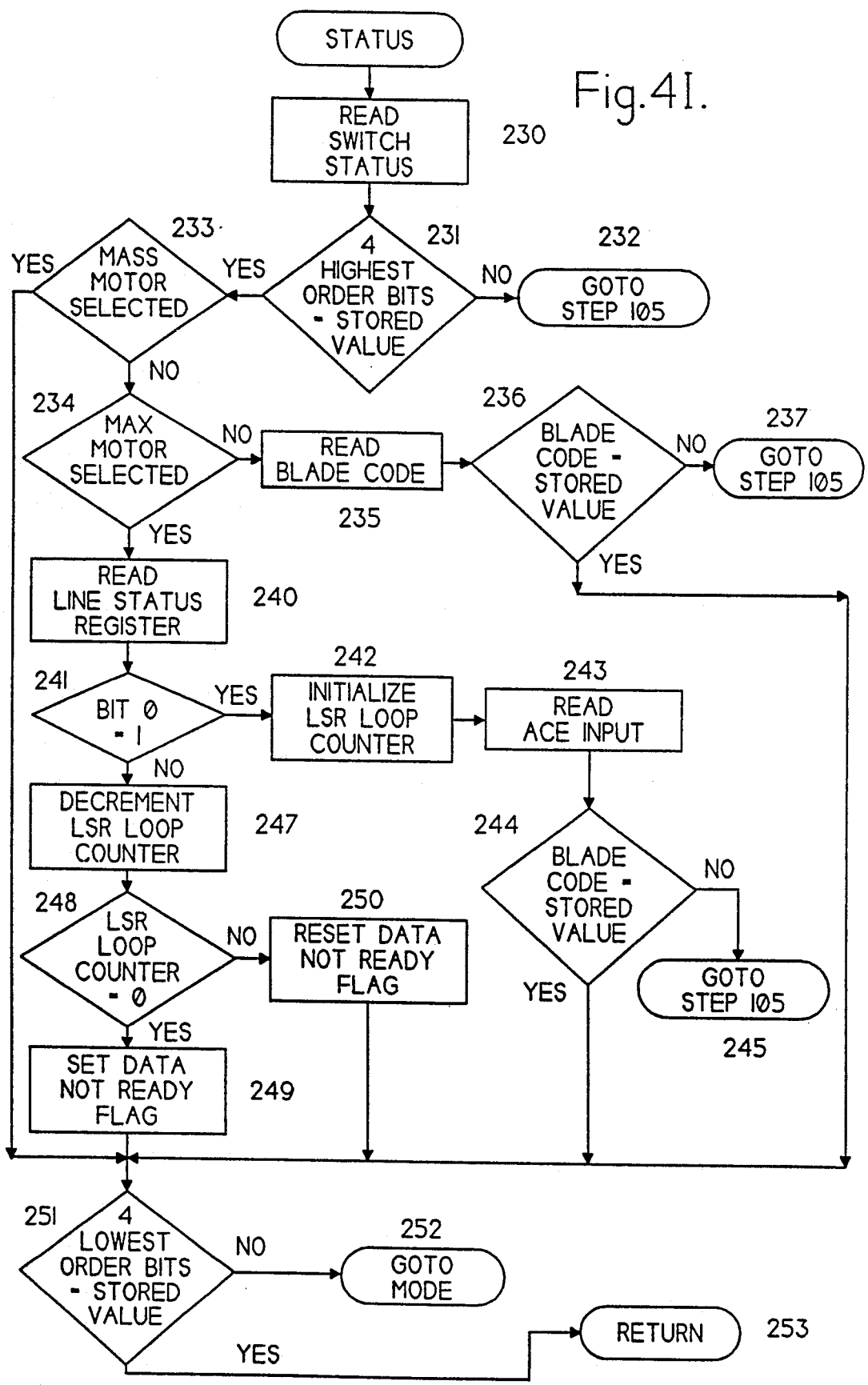
Figure 4K:
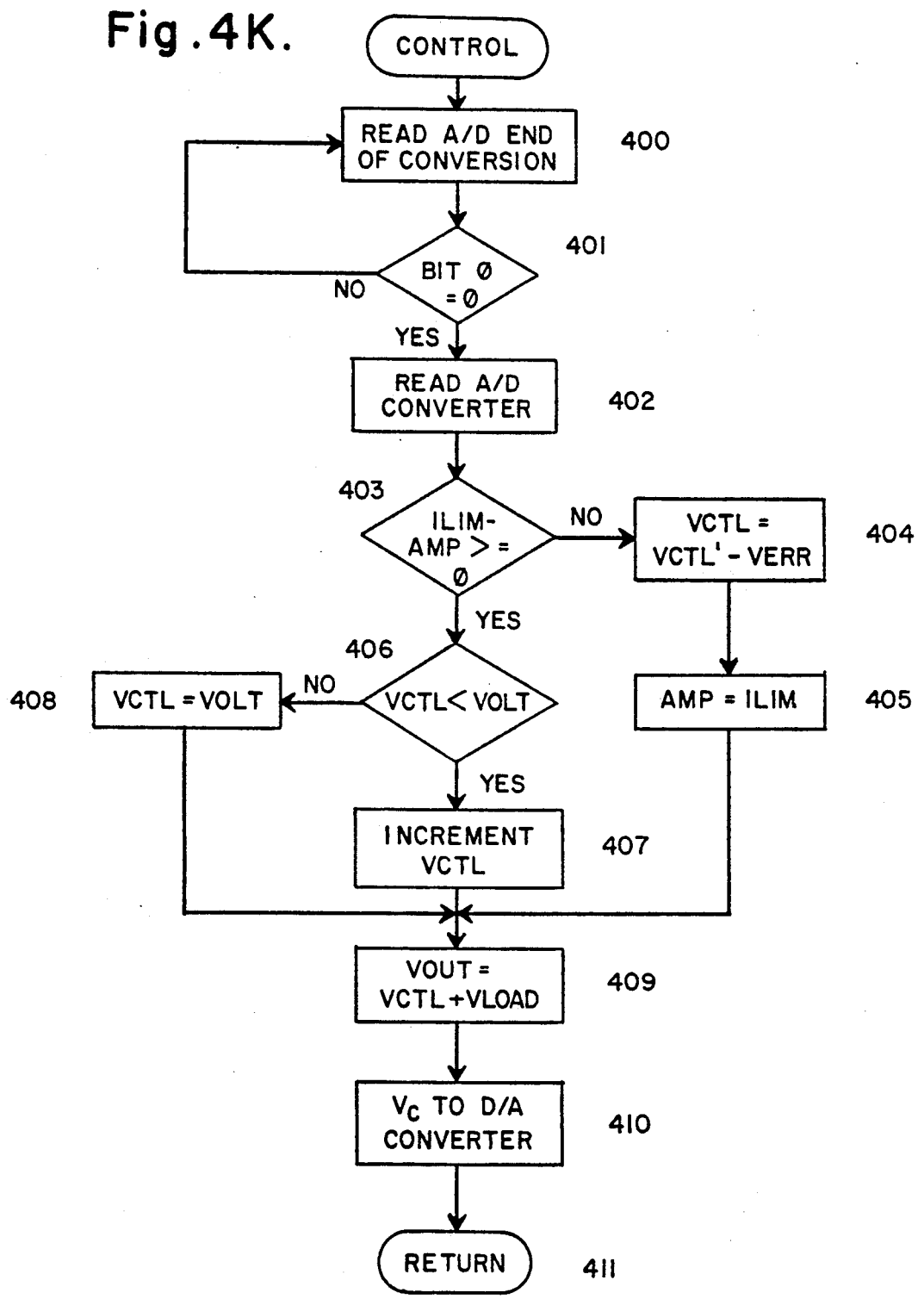
FIG. 4K depicts a flow chart illustrating the steps of subroutine CONTROL performed by the microprocessor of the system of FIG. 1.
Figure 4M:
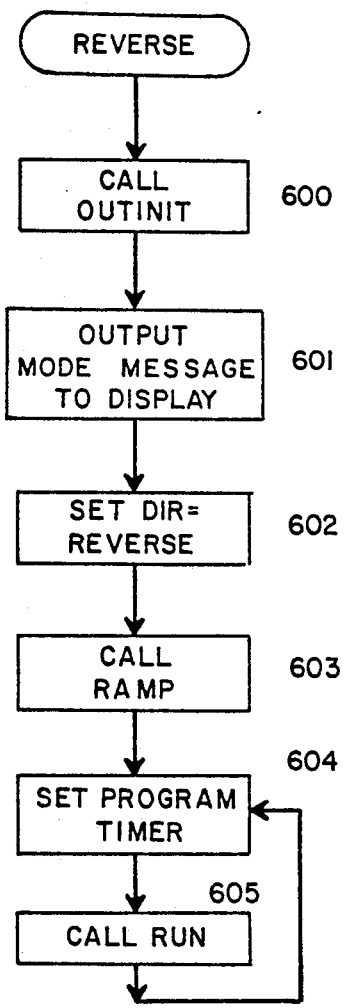
FIG. 4M depicts a flow chart illustrating the steps of motor control routine REVERSE performed by the microprocessor of the system of FIG. 1.
Figure 4N:
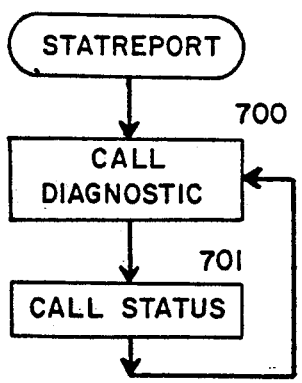
FIG. 4N depicts a flow chart illustrating the steps of motor control routine STATREPORT performed by the microprocessor of the system of FIG. 1.
Figure 4O:
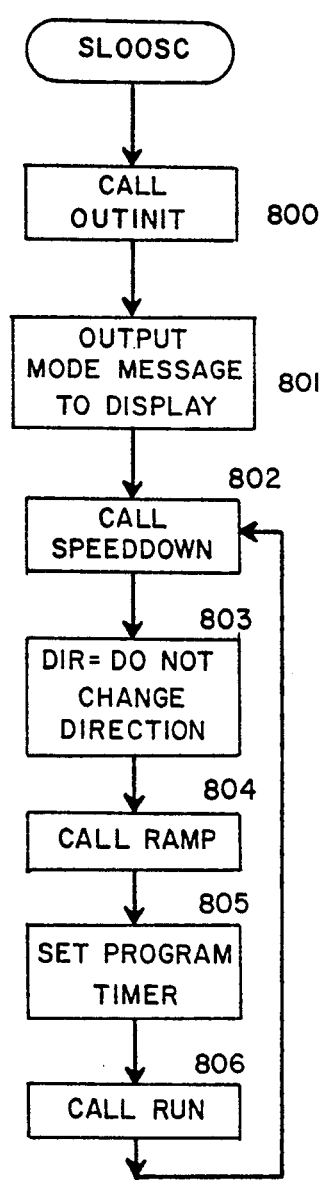
FIG. 4O depicts a flow chart illustrating the steps of motor control routine SLOOSC performed by the microprocessor of the system of FIG. 1.
Figure 4Q:
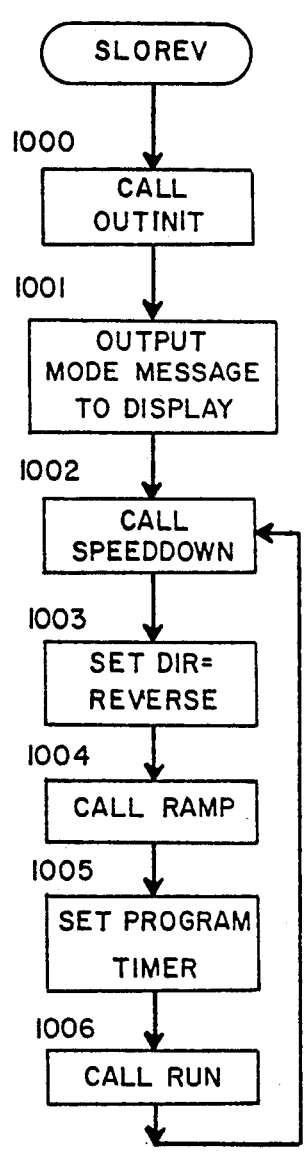
FIG. 4Q depicts a flow chart illustrating the steps of motor control routine SLOREV performed by the microprocessor of the system of FIG. 1.
Figure 4R:
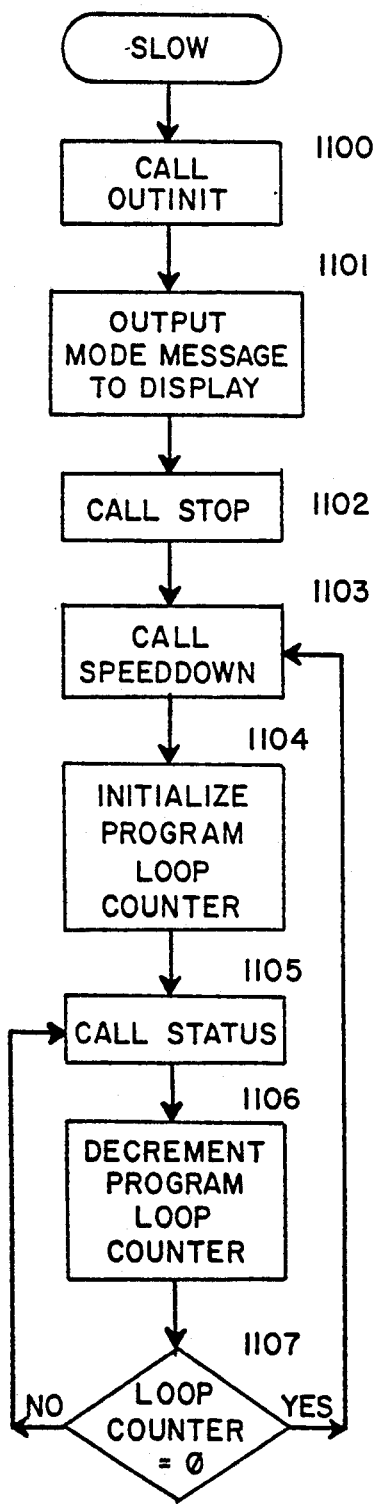
FIG. 4R depicts a flow chart illustrating the steps of motor control routine SLOW performed by the microprocessor of the system of FIG. 1.
Figure 4S:
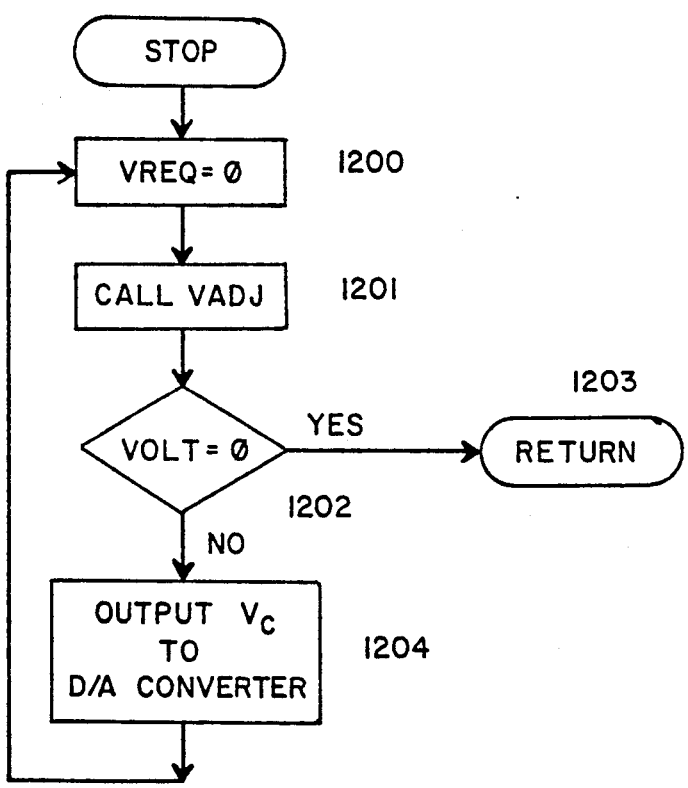
FIG. 4S depicts a flow chart illustrating the steps of motor control routine STOP performed by the microprocessor of the system of FIG. 1.
Figure 4T:
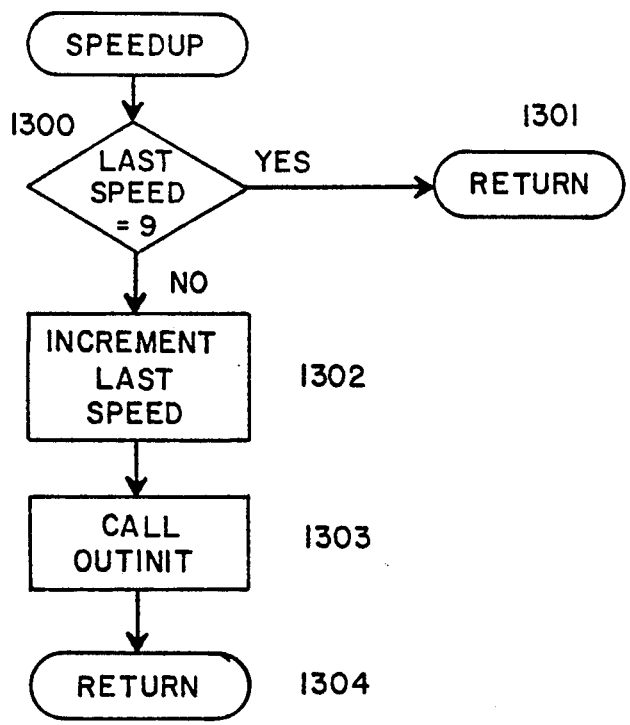
FIG. 4T depicts a flow chart illustrating the steps of subroutine SPEEDUP performed by the microprocessor of the system of FIG. 1.
Figure 4P:
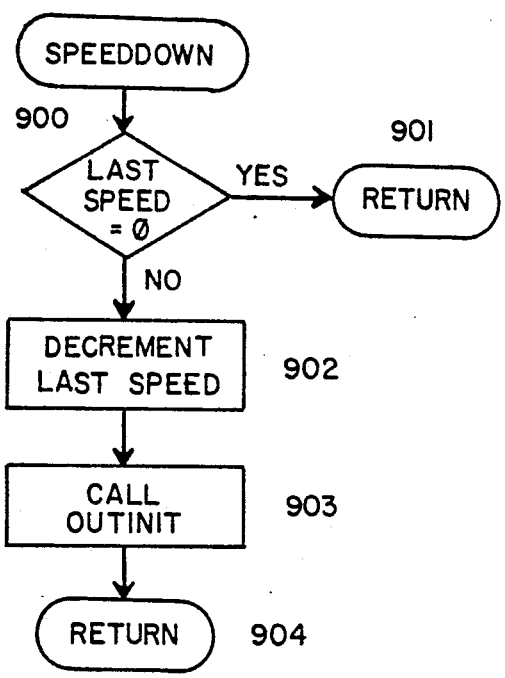
FIG. 4P depicts a flow chart illustrating the steps of subroutine SPEEDDOWN performed by the microprocessor of the system of FIG. 1.
Figure 4U:
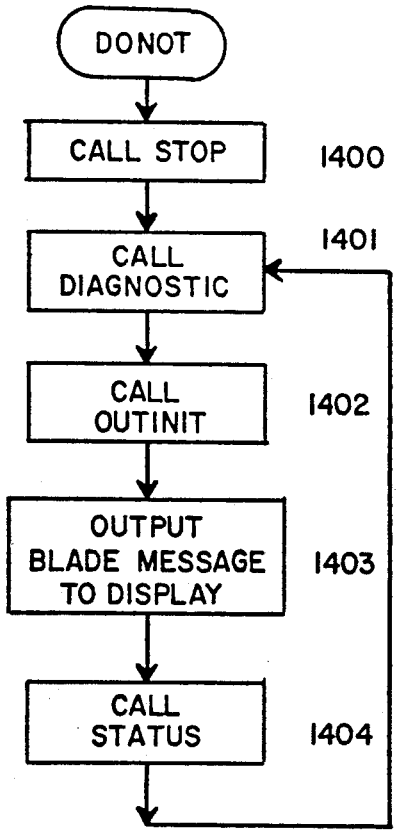
FIG. 4U depicts a flow chart illustrating the steps of motor control routine DONOT performed by the microprocessor of the system of FIG. 1.
Figure 4V:
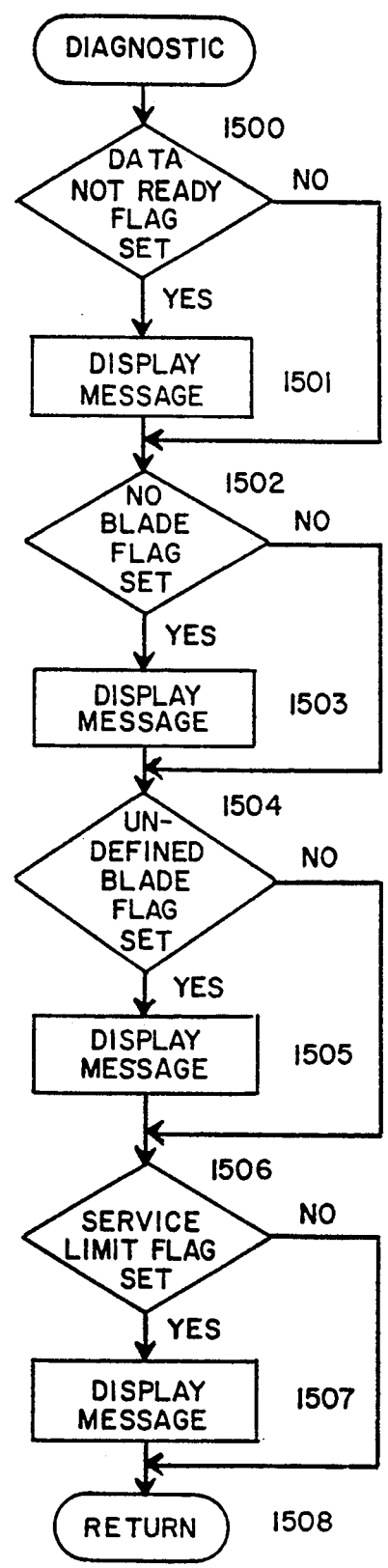
FIG. 4V depicts a flow chart illustrating the steps of subroutine DIAGNOSTIC performed by the microprocessor of the system of FIG. 1.

The operation of system 10 shown in FIG. 1 may be implemented as illustrated in the flow charts of FIGS. 4A–4V. The flow chart starts with the main routine BEGIN illustrated in FIG. 4A at step 100 where the microprocessor 20 of FIG. 1 performs an initialization routine to initialize system variables, turn off the direction control switch 16, zero the control signal $V_c$, initialize the ACE 36, turn off the display 78 and LEDs 46 and set the initial direction control switch 16 direction to "forward". Program control continues at step 101 where a procedure counter is incremented. The procedure counter serves to provide a mechanism to indicate to the user that routine maintenance of the system 10 is required. The procedure counter is compared, at step 102, to a decimal number such as "1000". If the procedure counter is greater than or equal to decimal "1000", program control continues with step 103 where a "service limit" diagnostic flag is set. A call to a subroutine DIAGNOSTIC in step 104 transfers program control to step 1500 shown in FIG. 4V.

Subroutine DIAGNOSTIC, shown in FIG. 4V, begins at step 1500 where the "data not ready" flag is checked to determine whether it has been set. If the "data not ready" flag has been set, program control continues with step 1501 where a message indicating that the data on the line status register is not valid is output to the display 78; otherwise program control is transferred to step 1502. The "no blade" flag is checked to determine whether it has been set in step 1502. If the "no blade" flag has been set, program control continues with step 1503 where a message indicating that no blade is presently inserted into the motor 11, 12 or 13 is output to the display 78; otherwise program control is transferred to step 1504. The "undefined blade" flag is checked to determine whether it has been set in step 1504. If the "undefined blade" flag has been set, program control continues with step 1505 where a message indicating that an unidentifiable blade is presently inserted into the motor 11, 12 or 13 is output to the display 78; otherwise program control is transferred to step 1506. The "service limit" flag is checked to determine whether it has been set in step 1506. If the "service limit" flag has been set, program control continues with step 1507 where a message indicating that routine servicing of the system 10 is required is output to the display 78; otherwise program control is transferred to step 1508. Program control is returned to the calling routine in step 1508.

Program control continues at step 105 if either the procedure counter is less than decimal "1000" in step 102 or after the return from the call to subroutine DIAGNOSTIC in step 104.

An n-bit switch status signal $V_{st}$ (which may be an eight-bit signal) consisting of inputs from motor selector switch 54, speed faster switch 56, speed slower switch 58, forward direction footswitch 60 and reverse direction footswitch 61 is read and the four highest order bits stored at step 105. The four highest order bits are designed to indicate which of the motors 11, 12 or 13 has been selected by the user through motor selector switch 54. The bit number assignments for MAX-motor 11, UMDU motor 12 and MASS motor 13 are indicated in the following table:

| Bit Number | Description |
|---|---|
| 7 | unused |
| 6 | UMDU motor |
| 5 | MASS motor |
| 4 | MAX motor |

The bit pattern of bit numbers four through seven of the eight-bit switch status signal $V_{st}$ is determined by the position of the motor selector switch 54 according to the following table:

| Inputs | | | | |
| --- | --- | --- | --- | --- |
| Bit 7 | Bit 6 | Bit 5 | Bit 4 | Switch Position |
| 1 | 0 | 1 | 1 | UMDU motor |
| 1 | 1 | 0 | 1 | MASS motor |
| 1 | 1 | 1 | 0 | MAX motor |

Bit six of the eight-bit switch status signal is tested at step 106. If bit six is equal to "0", program control continues with step 107 where program control is then transferred to subroutine UMDU at step 120 shown in FIG. 4B. If bit six is equal to "1", program control continues with step 108 where bit five of the eight-bit switch status signal $V_{st}$ is tested. If bit five is equal to "0", program control continues with step 109 where program control is transferred to subroutine MASS at step 130 shown in FIG. 4C. If bit five is equal to "1", program control continues with step 110 where bit four of the eight-bit switch status signal is tested. If bit four is equal to "0", program control continues with step 111 where program control is transferred to subroutine MAX at step 140 shown in FIG. 4D. If bit four is equal to "1", indicating that none of the motors 11, 12 or 13 have been selected through motor selector switch 54, program control returns to step 105 and the program loop consisting of steps 105, 106, 108 and 110 continues until a valid motor selection occurs.

When the determination is made at step 106 of FIG. 4A that the UMDU motor 12 has been selected, program control is transferred from step 107 of FIG. 4A to step 120 of FIG. 4B which illustrates the UMDU motor initialization subroutine. The blade code signal $V_b$ produced by the interface 35 of FIG. 1 is read by the microprocessor 20 and the two-bit blade code value stored in step 120. A list of all valid blade codes for the UMDU motor 12 and the corresponding blade descriptions is contained in the following table:

| SENSOR NUMBER | | |
| --- | --- | --- |
| 1 | 2 | BLADE DESCRIPTION |
| 1 | 1 | Inoperative |
| 1 | 0 | Small Joint |
| 0 | 1 | Shaver |
| 0 | 0 | Arty |

The blade code is compared to the decimal number "3" in step 121. If the blade code is equal to "3", the arthroscopic blade 42 is missing and the "no blade" diagnostic flag is set in step 122. If the blade code is not equal to "3", the "no blade" diagnostic flag is reset in step 123. In either case, program control continues with step 124 where a motor speed table pointer for the current blade 42 is initialized. The motor speed table pointer contains the address of the memory location which stores the speed at which the particular arthroscopic blade 42 currently inserted into the motor 11, 12 or 13 Was most recently operated. Consequently, a memory location is reserved for the forty-nine possible blades 42 which can be used with the MAX motor 11, the four possible blades 42 which can be used with the UMDU motor 12 and the one blade 42 which can be used with the MASS motor 13. This "last speed" data is stored in the non-volatile RAM 67 as an integer between "0" and decimal "9".

A blade data table pointer for the arthroscopic blade 42 currently inserted into the motor 11, 12 or 13 is initialized in step 125. All blade data and system control parameters are contained in fifty-four sequential data records of one hundred twenty-eight bytes each that represent all of the motor/blade combinations that the system 10 is configured to control. Certain of the blade data and system control parameters such as maximum and minimum speeds are available from either the blade or motor manufacturer. Other system control parameters such as the reference voltage VREF can be developed from operational characteristics provided by the blade and motor manufacturers through the application of well known principles governing the operation of DC motors. The blade data table pointer is calculated by mathematically manipulating the blade code to create an offset which is added to the base address of the data tables for the selected motor 11, 12 or 13. If the blade code is equal to the decimal number "3", in the case of the UMDU motor 12, or "0", in the case of the MAX motor 11 as described hereinbelow, indicating that no arthroscopic blade 42 is inserted into the UMDU motor 12 or MAX motor 11, the blade data table pointer will access system control parameters which will render UMDU motor 12 or MAX motor 11 inoperable. Program control is transferred, in step 126, to step 160 of FIG. 4E.

When the determination is made at step 108 in FIG. 4A that the MASS motor 13 has been selected, program control is transferred from step 109 of FIG. 4A to step 130 of FIG. 4C which illustrates the MASS motor initialization subroutine. The motor speed table pointer for the MASS motor 13 is initialized in step 130. The blade data table pointer for the MASS motor 13 is initialized in step 131. Program control is transferred, in step 132, to step 160 of FIG. 4E.

When the determination is made at step 110 in FIG. 4A that the MAX motor 11 has been selected, program control is transferred from step 111 in FIG. 4A to step 140 in FIG. 4D which illustrates the MAX motor initialization subroutine. A line status register loop counter is initialized to the decimal number "60" at step 140. A line status register indicates whether the data on the ACE 36 (which is the blade signal $V_b$) has been updated since the last time that data has been read from the ACE 36. In step 141, the line status register is read. Bit zero of the line status register is tested at step 142. If bit zero of the line status register is equal to "1", this indicates that the data on the ACE 36 has been updated since the last time that this device has been queried for data and a "data not ready" diagnostic flag is reset in step 143 with program control continuing at step 145. If bit zero does not equal "1" in step 142, the "data not ready" flag is set and a blade code, identifying the arthroscopic blade 42 which is currently inserted into the MAX motor 11 is set equal to "0" signifying that the data on the ACE 36 is not current and the identity of the arthroscopic blade 42 currently inserted into the MAX motor 11 is unknown. Program control is then transferred to step 146.

The blade code signal $V_b$, representing the blade code associated with the arthroscopic blade 42 currently inserted into the MAX motor 11, is read, in step 145, from the ACE 36. The blade code is compared, in step 146, to each of the entries in a "blade code look-up table" consisting of all valid blade codes. A sample list of some of the valid blade codes for the MAX motor 11 and the corresponding blade descriptions is contained in the following table:

| SENSOR NUMBER | | | | BLADE DESCRIPTION |
|---|---|---|---|---|
| 4 | 3 | 2 | 1 | |
| 1 | 10 | 01 | 00 | #48 7.0 Full Radius Reusable Blade |
| 1 | 10 | 00 | 10 | #47 Blade G |
| 1 | 10 | 00 | 01 | #46 6.5 Reusable Abrader |
| 1 | 10 | 00 | 00 | #45 4.5 Disposable Turbo Trimmer |

Step 147 determines whether the blade code has been found in the "blade code look-up table" and stores the location of the blade code match if such a match occurred. If the blade code has been found, an "undefined blade" diagnostic flag is reset in step 148; if the blade code has not been found, the "undefined blade" diagnostic flag is set in step 149. In either case, program control continues with step 150 where the blade code is compared to "0". If the blade code is equal to "0", indicating that the blade code has not been found in the "blade code look-up table" or that the data on the ACE 36 has not been updated thereby preventing the identification of the blade 42, a "no blade" diagnostic flag is set in step 152; if the blade code is not equal to "0", the "no blade" diagnostic flag is reset in step 151. In either case, program control continues with step 153, where the microprocessor 20 determines whether the "data not ready" diagnostic flag is set. If the "data not ready" flag is set, the "undefined blade" flag and the "no blade" flag are reset in step 154. If the "data not ready" flag is not set, or following step 154, program control continues with step 155 where the motor speed table pointer is initialized for the arthroscopic blade 42 which is currently inserted into the MAX motor 11. The blade data table pointer for the current blade 42 is initialized in step 156. Program control is transferred, in step 157, to step 160 of FIG. 4E.

2. Motor Control Routines

After the appropriate motor initialization routine has been performed, the eight-bit switch status signal $V_{st}$ is again read at step 160 of branch control routine MODE, shown in FIG. E, and the four lowest order bits stored. The four lowest order bits of the switch status signal correspond to the inputs at speed faster switch 56, speed slower switch 58, forward direction footswitch 60 and reverse direction footswitch 61. The following table indicates all possible combinations of these switch inputs and the corresponding motor control routine associated with each combination:

| Inputs | | | | Control | |
|---|---|---|---|---|---|
| Slower | Faster | Reverse | Forward | Routine | FIG. No. |
| 0 | 0 | 0 | 0 | Oscillate | (4F) |
| 0 | 0 | 0 | 1 | Reverse | (4M) |
| 0 | 0 | 1 | 0 | Forward | (4M) |
| 0 | 0 | 1 | 1 | Diagnostic Status | (4N) |
| 0 | 1 | 0 | 0 | Slow Down/ Oscillate | (4O) |
| 0 | 1 | 0 | 1 | Slow Down/ Reverse | (4Q) |
| 0 | 1 | 1 | 0 | Slow Down/ Forward | (4Q) |
| 0 | 1 | 1 | 1 | Slow Down | (4R) |
| 1 | 0 | 0 | 0 | Speed Up/ Oscillate | (4O) |
| 1 | 0 | 0 | 1 | Speed Up/ Reverse | (4Q) |
| 1 | 0 | 1 | 0 | Speed Up/ | (4Q) |

-continued

| Inputs | | | | Control | |
|---|---|---|---|---|---|
| Slower | Faster | Reverse | Forward | Routine | FIG. No. |
| 1 | 0 | 1 | 1 | Forward Speed Up | (4R) |
| 1 | 1 | 0 | 0 | Oscillate | (4F) |
| 1 | 1 | 0 | 1 | Reverse | (4M) |
| 1 | 1 | 1 | 0 | Forward | (4M) |
| 1 | 1 | 1 | 1 | Do Nothing | (4U) |

The four lowest order bits of the 8-bit switch status signal $V_{st}$ are mathematically manipulated in step 161 in a manner well known in the art in order to reference an address in a "jump table" which stores the branch address for the selected motor control routine. Program control is transferred to this branch address in step 162.

The various control routines may incorporate one or more of the following subroutines: OUTINIT discussed in conjunction with FIG. 4G, RAMP discussed in conjunction with FIG. 4H, STATUS discussed in conjunction with FIG. 4I, VADJ discussed in conjunction with FIG. 4J, CONTROL discussed in conjunction with FIG. 4K, RUN discussed in conjunction with FIG. 4L, SPEEDDOWN discussed in conjunction with FIG. 4P, SPEEDUP discussed in conjunction with FIG. 4T and DIAGNOSTIC discussed in conjunction with FIG. 4V.

a. Oscillate

The OSCILLATE motor control routine begins at step 190 in FIG. 4F with a call to the subroutine OUTINIT. Program control is transferred to step 200 shown in FIG. 4G where minimum speed LEDs 46 and maximum speed LEDs 46 are illuminated to display the minimum and maximum speeds at which arthroscopic blade 42 may operate. These minimum and maximum speeds are obtained from the appropriate locations in the blade data table. Control variables including a direction mask DMASK, a current limit ILIM and a motor resistance value R are also obtained from the blade data table in step 201. In step 202, a pointer is initialized to the appropriate address in the blade data table where a blade identification message is stored. Actual speed LEDS 46 are illuminated in step 203. The actual speed for the current arthroscopic blade 42 is obtained from the blade data table by indexing into the table according to the integer value stored in the motor speed data table for the current arthroscopic blade 42 in use. A reference voltage VREF, also corresponding to the integer value stored in the motor speed data table, is obtained, in step 204, from the blade data table by the same indexing method. Program control is returned to the calling routine in step 205.

Returning to FIG. 4F, a mode message indicating that the motor 11, 12 or 13 is currently in the "oscillate" mode is output to the display 78 in step 191. A "required direction" variable DIR is set, in step 192, to indicate that the current operating direction of the motor 11, 12 or 13 is not to be changed. A call to subroutine RAMP in step 193 transfers program control to step 210 shown in FIG. 4H. Subroutine RAMP provides controlled motor 11, 12 or 13 acceleration and deceleration in order to suppress electrical and mechanical transients.

The direction mask DMASK obtained from the blade data table in step 201 of FIG. 4G indicates whether a direction restriction requirement is associated with the particular blade 42 that is currently inserted into the motor 11, 12 or 13. The direction mask DMASK is compared to "0" in step 210 of FIG. 4H. If the direction mask DMASK is equal to "0", indicating that no direction restriction requirement exists, program control continues with step 212. If the direction mask DMASK is not equal to "0", the required direction DIR is set equal to the direction indicated in the direction mask DMASK in step 211 and program control continues with step 212. The present direction PDIR of the motor 11, 12 or 13 is compared to the required direction DIR in step 212. If the present direction PDIR is equal to the required direction DIR, program control continues with step 213; otherwise, program control continues with step 219. A call to the STATUS subroutine in step 213 transfers program control to step 230 of FIG. 4I.

The eight-bit switch status sign $V_{st}$ is read at step 230 shown in FIG. 4I. In step 231, the four highest order bits of the eight-bit switch status signal $V_{st}$ are compared to the four highest order bits of the eight-bit switch status signal $V_{st}$ which were stored in step 105 of FIG. 4A. If there is a difference in the four highest order bits between the stored value and the value read in step 230, program control is transferred, in step 232, to step 105 shown in FIG. 4A, i.e., the position of motor selector switch 54 has been changed thus necessitating initialization of a different motor 11, 12 or 13; otherwise program control continues with step 233. The determination is made, in step 233, whether the MASS motor 13 has been selected through motor selector switch 54. This determination is made by determining whether bit five of the eight-bit switch status signal $V_{st}$ has been set. If the MASS motor 13 has been selected, then program control continues at step 251 otherwise program control continues at step 234. The determination is made, in step 234, whether the MAX motor 11 has been selected through motor selector switch 54. This determination is made by determining whether bit four of the eight-bit switch status signal $V_{st}$ has been set If the MAX motor 11 has been selected, then program control continues at step 240; otherwise program control continues at step 235 where the two-bit blade code data for the UMDU motor 12 is read. In step 236, this blade code is compared to the blade code data stored in step 120 of FIG. 4B. If the blade code read in step 235 is the same as the stored blade code, program control continues with step 251; otherwise program control is transferred, in step 237, to step 105 of FIG. 4A, i.e., the arthroscopic blade 42 inserted into the UMDU motor 12 has been changed since the last blade identification has been performed thus necessitating the initialization of the UMDU motor 12 and arthroscopic blade 42.

If the determination is made in step 234 that the MAX motor 11 has been selected, the line status register is read in step 240. Bit zero of the line status register is compared to "1" in step 241. If bit zero is equal to "1", indicating that the blade code signal $V_b$ is ready on the ACE 36, then program control continues with step 242 where the line status register loop counter is initialized to decimal number "60". Program control then continues with step 243 where the blade code signal $V_b$ available on the ACE 36 is read and then proceeds to step 244 where the blade code is compared to the blade code data stored in step 145 of FIG. 4D. If the blade code read in step 243 is the same as the stored blade code, program control continues with step 251; otherwise program control is transferred, in step 245, to step 105 of FIG. 4A, i.e., the arthroscopic blade 42 inserted into the MAX motor 11 has been changed since the last blade identification has been performed thus necessitating the initialization of the MAX motor 11 and arthroscopic blade 42.

If bit zero of the line status register is not equal to "1" in step 241, which indicates that the blade code signal $V_b$ is not ready on the ACE 36, the line status register loop counter is decremented in step 247 and then compared to "0" in step 248. If the line status register loop counter is equal to "0", the "data not ready" diagnostic flag is set in step 249 and program control continues with step 251; otherwise the "data not ready" diagnostic flag is reset in step 250 and program control transferred to step 251.

The four lowest order bits of the eight-bit switch status signal $V_{st}$ read in step 230 are compared to the value of the four lowest order bits of the eight-bit switch status signal $V_{st}$ stored in step 160 of FIG. 4E. If there is no difference between the bit patterns, program control continues with step 253 which returns program control to the calling routine; otherwise program control is transferred, in step 252, to step 160 shown in FIG. 4E, i.e., at least one of switches 56, 58, 60 or 61 has produced a different input to eight-bit port 69 and a branch to a different motor control routine is required.

Returning to step 214 of FIG. 4H, a required voltage VREQ is set equal to the reference voltage VREF obtained in step 204 of FIG. 4G. Program control continues with step 215 with a call to subroutine VADJ which produces controlled ramping of the operating voltage to soften mechanical and electrical transients which may occur in motor 11, 12 or 13 operation. Program control is thus transferred to step 300 illustrated in FIG. 4J. A control voltage VOLT ($0 < = V_{OLT} < = V$-REF) is compared to the required voltage VREQ in step 300. If the two values are equal, program control is returned to the calling routine in step 301; otherwise program control continues with step 302 where the determination is made as to whether the control voltage VOLT is greater than the required voltage VREQ. If the control voltage VOLT is greater than the required voltage VREQ, then the control voltage VOLT is decremented in step 303. Program control is then returned to the calling routine in step 304. If the control voltage VOLT is less than the required voltage VREQ as determined in step 302, then the control voltage VOLT is incremented in step 305. Program control then continues with step 306 where program control is returned to the calling routine.

Returning to the flow chart of FIG. 4H, the required voltage VREQ is compared to the control voltage VOLT in step 216. If the two values are equal, program control is returned to the calling subroutine in step 217; otherwise program control continues with step 218 with a call to subroutine CONTROL and a transfer of program control to step 400 shown in FIG. 4K.

Subroutine CONTROL calculates the required operating voltage to be supplied to the motor 11, 12 or 13 through digital-to-analog converter 22. The same control algorithm services all three types of motors 11, 12 or 13. Two modes of motor control are possible. A "normal regulation mode" maintains the motor 11, 12 or 13 at a constant speed against variable loads up to the current limit ILIM point. A "current limit mode" regulates the actual motor current AMP to a fixed value, ILIM, determined by the individual motor 11, 12 or 13/arthroscopic blade 42 combination in use. This latter mode effects a mechanical torque limit for the purpose of protecting the arthroscopic blade 42 against mechanical failure.

In the normal operating mode, the output voltage VOUT required to control the motor 11, 12, or 13 within the current limit point ILIM can be shown by the equation:

$$\text{VOUT} = V_{CTL} + V_{LOAD} \tag{1}$$

where:
VOUT = output voltage to motor
VCTL = theoretical no-load output voltage required to operate the motor at any desired speed ($0 <= V_{CTL} <= \text{VOLT}$); at steady-state conditions, VCTL = VREF
VLOAD = AMP * R
AMP = the electrical current drawn by the motor (represented by $V_f$)
R = resistance value associated with the motor and control system In the current limiting mode the following equations are utilized to calculate the VCTL component of VOUT:

$$\text{VERR} = (\text{AMP} - \text{ILIM}) * R$$

$$\text{VCTL} = \text{VCTL}' - \text{VERR} \text{ (for all VCTL} >= 0) \tag{2}$$

where:
ILIM = the current limit point for the motor
AMP = the electrical current drawn by the motor (represented by $V_f$)
R = resistance value associated with the motor and control system
VCTL' = previous value of VCTL Step 400 of subroutine CONTROL is illustrated in FIG. 4K where an analog-to-digital converter "end of conversion" register is read. Bit zero of this register is compared to "0" in step 401. If bit zero is equal to "0", indicating that the required conversion is complete, then program control continues with step otherwise program control returns to step 400 and loops until the "end of conversion" is detected. The motor current level AMP is read at the analog-to-digital converter 18 input in step 402. The value of AMP is compared to the current limit ILIM for the particular motor 11, 12 or 13 and arthroscopic blade 42 in use in step 403. The value of ILIM was obtained in step 201 of FIG. 4G. If the motor current level AMP is less than or equal to the current limit ILIM, thus indicating that the "normal regulation mode" is appropriate, program control continues with step 406 where the control voltage VOLT is compared to VCTL, the theoretical no-load output voltage required to operate the motor 11, 12 or 13 at any desired speed ($0 <= \text{VCTL} <= \text{VOLT}$). If VCTL<VOLT in step 406, then VCTL is incremented in step 407 and program control continues with step 409; otherwise program control continues with step 408 where VCTL is set equal to VOLT and then continues with step 409.

If the motor current level AMP is greater than the current limit ILIM in step 403, indicating that the "current limit mode" is appropriate, then program control continues with step 404 where the theoretical no load output voltage VCTL is calculated according to equation (2) above. Program control then continues with step 405 where the motor current level AMP is set equal to the motor current limit ILIM. Program control continues with step 409 where VOUT is calculated according to equation (1) above. The control signal $V_c$, which is representative of VOUT, is then output to the digital-to-analog converter 22 in step 410. Program control is returned to the calling subroutine in step 411.

Returning to the flow chart of FIG. 4H, program control continues with step 213 upon the return from subroutine CONTROL which was called in step 218. If the present direction PDIR is not equal to the required direction DIR in step 212, program control continues with step 219 with a call to subroutine STATUS shown in FIG. 4I. The required voltage VREQ is set equal to "0" in step 220 and subroutine VADJ shown in FIG. 4J is called in step 221. The control voltage VOLT is compared to "0" in step 222 and if not equal to "0" program control continues with step 223 with a call to subroutine CONTROL shown in FIG. 4K. Program control continues with step 219 upon return from subroutine CONTROL. If the control voltage VOLT is equal to "0" in step 222, program control continues with step 224 where the direction of the direction switch 16 is reversed by outputting the appropriate polarity signal $V_p$. Program control then continues with step 213.

Returning to FIG. 4F, program control is returned to step 94, upon the return from the call to subroutine RAMP, where a program timer is set. Program control continues with step 195 where a call to subroutine RUN transfers program control to step 500. FIG. 4L illustrates the subroutine RUN where a call to the STATUS subroutine shown in FIG. 4I is performed in step 500. A call to the CONTROL subroutine shown in FIG. 4K is performed in step 501. The program timer is decremented in step 502 and then compared to "0" in step 503. If the program timer is equal to "0", program control is returned to the calling routine in step 504; otherwise program control is returned to step 500.

Returning to FIG. 4F, program control continues at step 196 where the direction variable DIR is set to change direction. Program control continues with step 193.

b. Reverse

Subroutine REVERSE, which causes the motor 11, 12 or 13 to operate in the reverse or counterclockwise direction, is shown in FIG. 4M and begins at step 600 with a call to subroutine OUTINIT shown in FIG. 4G. After the return from the call to this subroutine, program control continues with step 601 where a mode message indicating that the motor 11, 12 or 13 is currently in the "reverse" mode is output to the display 78. The direction variable DIR is set to "reverse" in step 602. Program control then continues with step 603 with a call to subroutine RAMP shown in FIG. 4H. After the return from this subroutine, program control continues with step 604 where a program timer is set. A call to subroutine RUN shown in FIG. 4L is initiated in step 605. After the return from subroutine RUN, program control is transferred back to step 604.

c. Forward

Subroutine FORWARD, which causes the motor 11, 12 or 13 to operate in the forward or clockwise direction, is identical to subroutine REVERSE shown in FIG. 4M except that a "forward" mode message is output in step 601 and step 602 is replaced by a step in which the direction variable DIR is set equal to "forward".

d. Diagnostic Status

Subroutine STATREPORT which provides a diagnostic status report is shown in FIG. 4N and begins at step 700 with a call to subroutine DIAGNOSTIC shown in FIG. 4V. After the return from the call to subroutine DIAGNOSTIC, program control continues with step 701 with a call to subroutine STATUS shown in FIG. 4I. Program control is transferred back to step 700 after the return from the call to subroutine STATUS.

e. Slow Down/Oscillate

FIG. 4O illustrates the SLOOSC subroutine which causes the motor 11, 12 or 13 to operate at a slower speed while oscillating. The subroutine begins at step 800 with a call to subroutine OUTINIT shown in FIG. 4G. A mode message indicating that the motor 11, 12 or 13 is currently in the "slow oscillate" mode is output to the display 78 in step 801. Subroutine SPEEDDOWN is called in step 802 where program control is transferred to step 900 shown in FIG. 4P. The integer value of the last speed in the motor speed table for the particular arthroscopic blade 42 currently in use is compared, in step 900 to "0". If the last speed in the motor speed table is equal to "0" program control continues with step 901 with a return to the calling routine; otherwise program control continues with step 902 where the last speed in the motor speed table is decremented. Program control continues with step 903 with a call to subroutine OUTINIT shown in FIG. 4G in order to determine the new value of the reference voltage VREF. Program control is returned to the calling routine in step 904.

Returning to FIG. 4O, program control continues with step 803 after the return from subroutine SPEEDDOWN. The direction variable DIR is set not to change direction in step 803. Program control continues with step 804 with a call to subroutine RAMP shown in FIG. 4H. After the return from the call to subroutine RAMP, a program timer is set in step 805. Program control continues with step 806 with a call to subroutine RUN shown in FIG. 4L. After the return from the call to subroutine RUN, program control is transferred back to step 802.

f. Slow Down/Reverse

Subroutine SLOREV which causes the motor 11, 12 or 13 to operate at a slower speed in the reverse or counterclockwise direction is illustrated in FIG. 4Q and begins at step 1000 with a call to subroutine OUTINIT shown in FIG. 4G. After the return from the call to subroutine OUTINIT, program control continues with step 1001 where a message indicating that the motor 11, 12 or 13 is operating in the "slow reverse" mode is output to the display 78. Program control continues with step 1002 with a call to subroutine SPEEDDOWN shown in FIG. 4P. After the return from the call to subroutine SPEEDDOWN, program control continues with step 1003 where the direction variable DIR is set to "reverse". A call to subroutine RAMP shown in FIG. 4H is initiated in step 1004. Program control continues, after the return from the call to subroutine RAMP, at step 1005 where a program timer is set. Subroutine RUN shown in FIG. 4L is called in step 1006. Program control is transferred back to step 1002 after the return from the call to subroutine RUN.

g. Slow Down/Forward

Subroutine SLOFOR which causes the motor 11, 12 or 13 to operate at a slower speed in the forward or clockwise direction is identical to subroutine SLOREV shown in FIG. 4Q except that a "slow forward" mode message is output in step 1001 and step 1003 is replaced by a step in which the direction variable DIR is set to "forward".

h. Slow Down

Subroutine SLOW which cause the motor 11, 12 or 13 to come to a complete stop and decrement the desired operating speed is shown in FIG. 4R and begins at step 1100 with a call to subroutine OUTINIT shown in FIG. 4G. After the return from the call to subroutine OUTINIT, program control continues with step 1101 where a message indicating that the motor 11, 12 or 13 is operating in the "slow" mode is output to the display 78. Program control then continues with step 1102 with a call to subroutine STOP shown in FIG. 4S. Program control is transferred to step 1200 where the required voltage VREQ is set equal to "0". A call is initiated to subroutine VADJ shown in FIG. 4J in step 1201. After the return from the call to subroutine VADJ, program control continues with step 1202 where the control voltage VOLT is compared to "0". If the control voltage VOLT is equal to "0" program control continues with step 1203 where program control is returned to the calling routine; otherwise program control continues with step 1204 where the control signal $V_c$, representative of the control voltage VOLT, is output to the digital-to-analog converter 22. Program control is transferred back to step 1200 following step 1204.

Returning to FIG. 4R, program control continues with step 1103, following the return from subroutine STOP, where a call is initiated to subroutine SPEEDDOWN shown in FIG. 4P. After the return from subroutine SPEEDDOWN, program control continues with step 1104 where a program loop counter is initialized to the decimal number "256". Program control continues with step 1105 with a call to subroutine STATUS shown in FIG. 4I. After the return from subroutine STATUS, program control continues with step 1106 where the program loop counter is decremented and then proceeds to step 1107 where the program loop counter is compared to "0". If the program loop counter is equal to "0", then program control is transferred back to step 1103; otherwise program control is transferred back to step 1105.

i. Speed Up/Oscillate

Subroutine FSTOSC causes the motor 11, 12 or 13 to operate at a faster speed while oscillating. Subroutine FSTOSC is identical to subroutine SLOOSC shown in FIG. 4O except that a mode message indicating that the motor drive unit 12 is currently in the "fast oscillate" mode is output to the display 78 in step 801 and the call to subroutine SPEEDDOWN in step 802 is replaced by a call to subroutine SPEEDUP which beings at step 1300 shown in FIG. 4T. The integer value of the last speed in the motor speed table for the particular arthroscopic blade 42 currently in use is compared, in step 1300 to decimal "9". If the last speed in the motor speed table is equal to "9", program control continues with step 1301 with a return to the calling routine; otherwise program control continues with step 1302 where the last speed in the motor speed table is incremented. Program control continues with step 1303 with a call to subroutine OUTINIT shown in FIG. 4G in order to determine the new value of the reference voltage VREF. Program control is returned to the calling routine in step 1304.

j. Speed Up/Reverse

Subroutine FSTREV, which cause the motor 11, 12 Or 13 to operate at a faster speed in the reverse or counterclockwise direction, is identical to subroutine SLOREV shown in FIG. 4Q except that a "fast reverse" mode message is output in step 1001 and the call to subroutine SPEEDDOWN in step 1002 is replaced by a call to subroutine SPEEDUP shown in FIG. 4T.

k. Speed Up/Forward

Subroutine FSTFOR, which causes the motor 11, 12 or 13 to operate at a faster speed while in the forward or clockwise direction, is identical to subroutine SLOREV shown in FIG. 4Q except that a "fast forward" mode message is output in step 1001, step 1003 is replaced by a step in which the direction variable DIR is set to "forward" and the call to subroutine SPEEDDOWN in step 1002 is replaced by a call to subroutine SPEEDUP shown in FIG. 4T.

l. Speed Up

Subroutine FAST, which causes the motor 11, 12 Or 13 to come to a complete stop and increments the desired operating speed, is identical to subroutine SLOW shown in FIG. 4R except that a "fast" mode message is output in step 1101 and step 1103 is replaced by a step which initiates a call to subroutine SPEEDUP shown in FIG. 4T.

m. No Action

Subroutine DONOT which causes the motor 11, 12 or 13 to come to a complete stop begins at step 1400 shown in FIG. 4U with a call to subroutine STOP shown in FIG. 4S. Program control continues, after the return from subroutine STOP with step 1401 and a call to subroutine DIAGNOSTIC shown in FIG. 4V. After the return from the call to subroutine DIAGNOSTIC, program control continues with step 1402 with a call to subroutine OUTINIT shown in FIG. 4G. The blade message obtained from the blade data table in step 202 of FIG. 4G is output to display 78 in step 1403. Program control continues with a call to subroutine STATUS shown in FIG. 4I in step 1404. Program control is transferred back to step 1401 after the return from the call to subroutine STATUS.

While the present invention has been described in connection with an exemplary embodiment thereof, it will be understood that many modifications and variations will be readily apparent to those of ordinary skill in the art. This disclosure and the following claims are intended to cover all such modifications and variations.

I claim:

1. An apparatus for controlling the speed of a plurality of DC motors, comprising:
   means for supplying voltage to one of the plurality of DC motors;
   means for selecting one of the DC motors to be connected to said means for supplying voltage;
   means for selecting a desired speed for the selected DC motor;
   means for selecting a desired mode of operation for the selected DC motor;
   means for producing a feedback signal representative of an electrical current drawn by the selected DC motor; and
   control means for:
      (i) producing a reference voltage in response to said means for selecting one of the DC motors and said means for selecting said desired speed;
      (ii) producing a control voltage in response to said reference voltage and said means for selecting said desired mode of operation;
      (iii) producing a load voltage in response to said feedback signal and said means for selecting one of the DC motors; and
      (iv) outputting a control signal which is the sum of said control voltage and said load voltage to said means for supplying voltage.

2. The apparatus of claim 1 wherein said control means produces said reference voltage by selecting a value from a look-up table.

3. The apparatus of claim 2 wherein said control means produces said load voltage by multiplying said feedback signal by a resistance value.

4. The apparatus of claim 3 additionally comprising means for operatively connecting a tool to the selected DC motor and means for producing a tool code signal representative of the connected tool and wherein said control means selects said reference voltage based on said tool code, said means for selecting one of the DC motors and said means for selecting said desired speed.

5. The apparatus of claim 4 wherein said selected reference voltage is within predetermined maximum and minimum limits so that the DC motor is operated between maximum and minimum speeds.

6. The apparatus of claim 4 wherein said control means selets said resistance value based on said tool code, said means for selecting one of the DC motors and said means for selecting said desired spped.

7. The apparatus of claim 6 wherein said control means additionally selects a current limit value based on said tool code, said means for selecting one of the DC motors and said means for selecting said desired speed and wherein said load voltage is produced by multiplying said current limit value by said resistance value and wherein said selected reference voltage is modified by subtracting from it the product of said resistance value and the difference between said feedback signal and said current limit value when said feedback signal exceeds said current limit value.

8. The apparatus of claim 4 additionally comprising means for controlling the plurality of the voltage applied to the selected DC motor and wherein said control means additionally selects a motor direction restriction based on said tool code, said means for selecting one of the DC motors and said means for selecting said desired speed and outputs a polarity signal to said polarity control means for controlling the direction of rotation of said motor.

9. The apparatus of claim 4 wherein said means for producing said tool code signal includes magnets attached to the tool and magnetic sensing devices attached to the motor.

10. The apparatus of claim 9 wherein said magnetic sensing devices include a plurality of Hall-effect devices.

11. The apparatus of claim 9 wherein said magnetic sensing devices include a plurality of reed switches.

12. The apparatus of claim 9 wherein the number of said magnets and their magnetic polar orientation constitute a pattern unique to each type of tool.

13. The apparatus of claim 4 additionally comprising first diagnostic means for indicating that said tool code signal has not changed since the last time it was read by said control means.

14. The apparatus of claim 13 additionally comprising second diagnostic means for indicating that said tool code signal is unidentifiable.

15. The apparatus of claim 14 additionally comprising third diagnostic means for indicating that said tool code signal indicates that no tool is inserted into the selected DC motor.

16. The apparatus of claim 15 additionally comprising means for counting the number of times the apparatus has been operated and fourth diagnostic means responsive to said means for counting for indicating that the apparatus requires routine maintenance procedures.

17. The apparatus of claim 4 additionally comprising means for storing the last speed at which the selected DC motor and tool operatively coupled thereto were operated.

18. The apparatus of claim 17 wherein said means for storing the last speed includes a nonvolatile RAM.

19. The apparatus of claim 8 wherein said control means outputs said polarity signal so as to operate the selected DC motor in an oscillating mode such that the motor is operated at a given speed in one direction for a predetermined period of time then operated in the opposite direction at the same speed for an identical period of time.

20. The apparatus of claim 2 wherein said control means selects increasing and decreasing values for said reference voltage so as to soften any mechanical and electrical transients in the motor operation.

21. A system for controlling powered surgical instruments within predetermined parameters, comprising:
   means for supplying voltage to one of a plurality of hand-held surgical motors;
   means for selectively connecting one of the surgical motors to said means for supplying voltage;
   means for selecting a desired speed for the connected surgical motor;
   means for selecting a desired mode of operation for the connected surgical motor;
   means for producing a feedback signal representative of an electrical current drawn by the connected surgical motor; and
   control means for:
      (i) selecting a reference voltage in response to the connected surgical motor and said desired speed;
      (ii) producing a control voltage in response to said reference voltage and said means for selecting said desired mode of operation;
      (iii) producing a load voltage in response to said feedback signal and the connected surgical motor; and
      (iv) outputting a control signal responsive to said control voltage and said load voltage to said means for supplying voltage.

22. The apparatus of claim 21 wherein the predetermined parameters include constant speed, a maximum speed limit, a minimum speed limit and a current limit.

23. The apparatus of claim 22 wherein said desired speed is maintained constant at varying loads by changing the value of said load voltage.

24. The apparatus of claim 22 wherein said desired speed is maintained within said maximum and minimum speed limits by proper selection of said reference voltage.

25. The apparatus of claim 22 wherein the current drawn by the connected motor is maintained below said current limit by reducing the value of said reference voltage when the current drawn by the motor exceeds said current limit.

26. A method for controlling the speed of a plurality of DC motors, comprising the steps of:
   selectively to one of the plurality of DC motors;
   selecting a desired speed for the selected DC motor;
   producing a feedback signal representative of an electrical current drawn by the selected DC motor;
   producing a reference voltage in response to the selected DC motor and said desired speed;
   producing a control voltage in response to said reference voltage and said desired mode of operation;
   producing a load voltage in response to said feedback signal and the selected DC motor; and
   outputting a control signal which is the sum of said control voltage and said load voltage to said means for supplying voltage.

27. The apparatus of claim 18 additionally comprising means for recalling the last speed at which the selected DC motor and tool operatively coupled thereto were operated from said nonvolatile RAM.

* * * * *

UNITED STATES PATENT AND TRADEMARK OFFICE
CERTIFICATE OF CORRECTION

PATENT NO. : 5,077,506
DATED : December 31, 1991
INVENTOR(S) : Kenneth W. Krause It is certified that error appears in the above-identified patent and that said Letters Patent is hereby corrected as shown below:

Col. 1, line 26, after "limits", insert --.--.

Col. 1, line 41, after "controlled", insert --.--.

Col. 3, line 36, after "FIG. 1;", begin a new paragraph with "FIG. 4U".

Col. 3, line 39, after "and", begin a new paragraph with "FIG. 4V".

Col. 4, line 2, after "invention", insert --.--.

Col. 4, line 4, after "ments", insert --.--.

Col. 4, line 64, delete "sensors," and substitute --sensors'-- therefor.

Col. 5, line 11, delete "4" and substitute --44-- therefor.

Col. 5, line 26, delete "1" and substitute --11-- therefor.

UNITED STATES PATENT AND TRADEMARK OFFICE
CERTIFICATE OF CORRECTION

PATENT NO. : 5,077,506

DATED : December 31, 1991

INVENTOR(S) : Kenneth W. Krause

It is certified that error appears in the above-identified patent and that said Letters Patent is hereby corrected as shown below:

Col. 5, line 46, after "$V_{st}$", insert a space.

Col. 7, line 11, after "signal", insert --$V_{st}$--.

Col. 7, line 22, after "signal", insert --$V_{st}$--.

Col. 7, line 61, delete "Was" and substitute --was-- therefor.

Col. 9, line 43, delete "E," and substitute --4E,-- therefor.

Col. 9, line 44, after "signal", insert --$V_{st}$--.

Col. 11, line 15, delete "sign" and substitute --signal-- therefor.

Col. 11, line 32, after "251", insert --;--.

Col. 11, line 37, after "set", insert --.--.

Col. 12, line 3, after ""1", insert --"--.

Col. 12, line 4, delete """.

UNITED STATES PATENT AND TRADEMARK OFFICE
CERTIFICATE OF CORRECTION

PATENT NO. : 5,077,506

DATED : December 31, 1991

INVENTOR(S) : Kenneth W. Krause

It is certified that error appears in the above-identified patent and that said Letters Patent is hereby corrected as shown below:

Col. 12, lines 32-33, delete "$0<=V_{OLT}<=V-REF$" and substitute --$0 <= VOLT <= VREF$-- thereror.

Col. 13, line 5, delete "$VOUT=V_{CTL} + VLOAD$  (1)" and substitute --(1) $VOUT = VCTL + VLOAD$-- therefor.

Col. 13, line 11, delete "$(0<=V_{cTl} =VOLT)$" and substitute --$(0 <= VCTL <= VOLT)$-- therefor.

Col. 13, line 25, delete "$VCTL = VCTL - VERR$ (for all $VCTL>=0$)   (2)" and substitute --(2) $VCTL = VCTL' - VERR$ (for all $VCTL >= 0$)-- therefor.

Col. 13, line 39, after "step", insert --402;--.

Col. 14, line 13, after "0", second occurence, insert --,--.

Col. 14, line 24, delete "94" and substitute --194-- therefor.

Col. 16, line 2, delete "cause" and substitute --causes-- therefor.

UNITED STATES PATENT AND TRADEMARK OFFICE
CERTIFICATE OF CORRECTION

PATENT NO. : 5,077,506

DATED : December 31, 1991

INVENTOR(S) : Kenneth W. Krause

It is certified that error appears in the above-identified patent and that said Letters Patent is hereby corrected as shown below:

Col. 16, line 65, delete "Or" and substitute --or-- therefor.

Col. 17, line 13, delete "1." and substitute --l.-- therefor.

Col. 17, line 14, delete "Or" and substitute --or-- therefor.

Col. 18:
Claim 6, line 22, delete "selets" and substitute --selects-- therefor.

Claim 6, line 24, delete "spped" and substitute --speed-- therefor.

Col. 19:
Claim 20, line 21, delete "reference", insert --control--.

Col. 20:
Claim 26, line 24, after "selectively", insert --supplying voltage--.

Claim 26, between lines 25, and 26, insert --selecting a desired mode of operation for the selected DC motor;--.

UNITED STATES PATENT AND TRADEMARK OFFICE
CERTIFICATE OF CORRECTION

PATENT NO. : 5,077,506

DATED : December 31, 1991

INVENTOR(S) : Kenneth W. Krause

It is certified that error appears in the above-indentified patent and that said Letters Patent is hereby corrected as shown below:

Column 5, line 27, delete "1" and insert --11--.

Signed and Sealed this

Ninth Day of November, 1993

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,077,506

DATED : December 31, 1991

INVENTOR(S) : Kenneth W. Krause

It is certified that error appears in the above-indentified patent and that said Letters Patent is hereby corrected as shown below:

Col. 3, line 61, delete "i." and substitute --j.-- therefor.

Col. 3, line 62, delete "j." and substitute --k.-- therefor.

Col. 3, line 63, delete "k." and substitute -- l.-- therefor.

Col. 3, line 64, delete "l." and substitute -- m.-- therefor.

Col. 16, line 49, delete "beings" and substitute --begins-- therefor.

Col. 16, line 64, delete "cause" and substitute --causes-- therefor.

Signed and Sealed this

Twenty-second Day of February, 1994

Attest:

BRUCE LEHMAN

*Attesting Officer*     *Commissioner of Patents and Trademarks*